US009161928B2

(12) United States Patent
Escriba Ruiz et al.

(10) Patent No.: US 9,161,928 B2
(45) Date of Patent: Oct. 20, 2015

(54) USE OF DERIVATIVES OF POLYUNSATURATED FATTY ACIDS AS MEDICAMENTS

(75) Inventors: Pablo Vicente Escriba Ruiz, Palma de Mallorca (ES); Xavier Busquets Xaubet, Palma de Mallorca (ES); Silvia Teres Jimenez, Palma de Mallorca (ES); Gwendolyn Barcelo Coblijn, Palma de Mallorca (ES); Victoria Llado Canellas, Palma de Mallorca (ES); Amaia Marcilla Etxenike, Palma de Mallorca (ES); Maria Laura Martin, Palma de Mallorca (ES); Monica Higuera Urbano, Palma de Mallorca (ES); Rafael Alvarez Martinez, Palma de Mallorca (ES); Daniel Horacio Lopez, Palma de Mallorca (ES)

(73) Assignee: Lipopharma Therapeutics, S.L., Palma de Mallorca (ES)

(*) Notice: Subject to any disclaimer, the term of this patent is extended or adjusted under 35 U.S.C. 154(b) by 904 days.

(21) Appl. No.: 13/257,128

(22) PCT Filed: Mar. 15, 2010

(86) PCT No.: PCT/ES2010/070153
§ 371 (c)(1),
(2), (4) Date: Nov. 28, 2011

(87) PCT Pub. No.: WO2010/106211
PCT Pub. Date: Sep. 23, 2010

(65) Prior Publication Data
US 2012/0108550 A1    May 3, 2012

(30) Foreign Application Priority Data
Mar. 16, 2009    (ES) .................................. 200900725

(51) Int. Cl.
A61K 31/20    (2006.01)
(52) U.S. Cl.
CPC ....................... A61K 31/20 (2013.01)
(58) Field of Classification Search
USPC ................. 554/224, 109; 514/109, 560, 550; 544/224, 109
IPC ....................................................... A61K 31/20
See application file for complete search history.

(56) References Cited

U.S. PATENT DOCUMENTS

| 7,550,613 | B2 * | 6/2009 | Bryhn et al. | 554/85 |
| 7,799,782 | B2 * | 9/2010 | Munson et al. | 514/234.5 |
| 2006/0166935 | A1 | 7/2006 | Bryhn et al. | |
| 2007/0088170 | A1 * | 4/2007 | Bryhn et al. | 554/62 |

FOREIGN PATENT DOCUMENTS

| EP | 1772146 A1 | 4/2007 |
| ES | 2161146 A1 | 11/2001 |
| WO | WO 2006/067498 A1 | 6/2006 |
| WO | WO 2007/058523 A1 | 5/2007 |
| WO | WO 2008/053331 A1 | 5/2008 |

OTHER PUBLICATIONS

Bryhn et al. CAS: 145: 483779, 2006.*
Van et al. CAS: 86: 53082, 1977.*
Grundmann et al. CAS: 141: 309671, 2004.*
Wang et al. CAS: 142: 468998, 2004.*
Barbosa et al. CAS: 146: 479013, 2006.*
Parkkari et al. CAS: 144: 467920, 2006.*
Poop et al. CAS: 146: 33041, 2006.*
Alemany, R. et al., 2-Hydroxyoleic Acid A New Hypotensive Molecule. Hypertension vol. 43, 249-254 (2004), American Heart Association (USA).
Alemany, R. et al., G protein-coupled receptor systems and their lipid environment in health disorders during aging. Biochim. Biophys. Acta, vol. 1768, 964-975 (2007). Elsevier (Netherlands).
Buda, C. et al., Structural order of membranes and composition of phospholipids in fish brain cells during thermal acclimatization. Proc. Natl. Acad. Sci. USA, vol. 91, 8234-8238 (1994). National Academy of Sciences (United States).
Coles, B. et al., Nitrolinoleate Inhibits Platelet Activation by Attenuating Calcium Mobilization and Inducing Phosphorylation of Vasodilator-stimulated Phosphoprotein through Elevation of cAMP, J. Biol. Chem., vol. 277, 8832-8840 (2002). American Society for Biochemistry and Molecular Biology (United Sates).
Escriba, P.V. et al., Disruption of cellular signaling pathways by daunomycin through destabilization of nonlamellar membrane structures, Proc. Natl. Acad. Sci USA, vol. 92, 7595-7599 (1995). National Academy of Sciences (United States).
Escriba, P.V. et al., Role of lipid polymorphism in G protein-membrane interactions: Nonlamellar-prone phospholipids and peripheral protein binding to membranes, Proc. Natl. Acad. Sci USA., vol. 94 11375-11380 (1997). National Academy of Sciences (United States).
Escriba, P.V. et al., Alteration of Lipids, G Proteins, and PKC in Cell Membranes of Elderly Hypertensives, Hypertension, vol. 41, 176-182 (2003), American Heart Association (USA).
Escriba, P.V., Membrane-lipid therapy: a new approach in molecular medicine, Trends. Mol. Med., vol. 12, 34-43 (2006). Elsevier Science Ltd. (Great Britain).
Escriba, P.V. et al., Membranes: a meeting point for lipids, proteins and therapies, J. Cell. Mol. Med., vol. 12, 829-875 (2008). Wiley-Blackwell (Great Britain).

(Continued)

*Primary Examiner* — Rei-Tsang Shiao
(74) *Attorney, Agent, or Firm* — Sterne, Kessler, Goldstein & Fox P.L.L.C.

(57) ABSTRACT

Use of polyunsaturated fatty acid derivatives as medicaments or functional foods. The present invention relates to the use of 1,2-fatty acid derivatives in the treatment or prevention of common diseases whose etiology is based on alterations (of any type) of the cell membrane lipids, for example, changes in levels, in the composition or in the structure of these lipids. In addition, for diseases in which the regulation of lipid composition and of the structure of the membranes (or proteins that interact with membranes) causes the reversion of pathological state.

13 Claims, 9 Drawing Sheets

(56) References Cited

OTHER PUBLICATIONS

Florent, S. et al., Docosahexaenoic acid prevents neuronal apoptosis induced by soluable amyloin-β oligomers, J. Neurochem., vol. 96, 385-395 (2006). Blackwell Science (Great Britain).
Folch, J. et al., Preparation of Lipide Extracts from Brain Tissue, J. Biol. Chem., vol. 191, 833-841 (1951). American Society for Biochemistry and Molecular Biology (United States).
Jackson, C.L. and Schwartz, S.M., Pharmacology of Smooth Muscle Cell Replication, Hypertension, vol. 20, 713-736 (1992). American Heart Association (USA).
Jung, U.J. et al., n-3 Fatty Acids and cardiovascular disease: mechanisms underlying beneficial effects, Am. J. Clin. Nutr., vol. 87, 2003S-9S (2008). American Society of Clinical Nutrition (United States).
Lane, R.M. and Farlow, M.R., Lipid homeostasis and apolipoprotein E in the development and progression of Alzheimer's disease, J. Lipid. Res., vol. 46, 949-968 (2005). American Society for Biochemistry and Molecular Biology (United States).
Martinez, J. et al., Membrane Structure Modulation, Protein Kinase Cα Activation and Anticancer Activity of Minerval, Mol. Pharmcol., vol. 67 531-540 (2005). American Society for Pharmacology and Experimental Therapeutics (United States).
Rapoport, S.I., Brain arachidonic and docosahexaenoic acid cascades are selectively altered by drugs, diet and disease, Prostaglandins Leukot. Essent. Fatty Acids, vol. 79, 153-156 (2008). Churchill Livingstone (Great Britain).
Sagin, F.G. and Sozmen, E.Y., Lipids as key players in Alzheimer disease: alterations in metabolism and genetics, Curr. Alzheimer Res., vol. 5, 4-14 (2008). Bentham Science Publishers (United States).
Schwartz, S.M. et al., Replication of Smooth Muscle Cells in Vascular Disease, Circ. Res., vol. 58, 427-444 (1986). Lippincott Williams & Wilkins (United States).
Stender, S. and Dyerberg, J., Influence of trans fatty acids on health, Ann. Nutr. Metab., vol. 48, 61-66 (2004). Karger (United States).
Teres, S. et al., Oleic acid content is responsible for the reduction in blood pressure induced by olive oil, Proc. Natl. Acad. Sci. USA, vol. 105, 13811-13816 (2008). National Academy of Sciences (United States).
Trombetta, A. et al., Arachidonic and docosahexaenoic acids reduce the growth of A549 human lung-tumor cells increasing lipid peroxidation and PPARs, Chem. Biol. Interact., vol. 165, 239-250 (2007). Elsevier (Netherlands).
Vögler, O. et al., The Gβγ Dimer Drives the Interaction of Heterotrimeric Gi Proteins with Nonlamellar Membrane Structures, J. Biol. Chem., vol. 279, 36540-36545 (2004). American Society for Biochemistry and Molecular Biology (United States).
Vögler, O. et al., Membrane interactions of G proteins and other related proteins, Biochim. Biophys Acta, vol. 1778, 1640-1652 (2008). Elsevier (Netherlands).
Yang, Q. et al., Influence of the Membrane Lipid Structure on Signal Processing via G Protein-Coupled Receptors, Mol. Pharmacol., vol. 68, 210-217 (2005). American Society for Pharmacology and Experimental Therapeutics (United States).
Bohannon, M.B. et al., Unsaturated C18 alfa-hydroxy acids in Salvia Nilotica, Lipids, vol. 10, 703-706 (1975), Springer International Publishing AG (Germany).
Larsen, L.N. et al., Alpha and Beta Alkyl-Substituted Eicosapentaenoic Acids: Incorporation into Phospholipids and Effects on Prostaglandin H Synthase and 5-Lipoxygenase, Biochem. Pharm., vol. 55, 405-411 (1998). Elsevier (Netherlands).
Martin, M.L. et al, Minerval (2-hydroxyoleic acid) may replace oleic acid in human tumor cell lines, Chem. Phys. Lipids, vol. 1545 (Supplement), S48 (2008). Elsevier (Netherlands).
Rossmeisl, M. et al, Prevention and Reversal of Obesity and Glucose Intolerance in Mice by DHA Derivatives, Obesity, vol. 17, 1023-1031 (2009). Nature Publishing Group (United Kingdom).
Vögler, O. et al., Structure-Effect Relation of C18 Long-Chain Fatty Acids in the Reduction of Body Weight in Rats, Int. J. Obes., vol. 32, 464-473 (2008). Nature Publishing Group (United Kingdom).

* cited by examiner

FIGURE 2
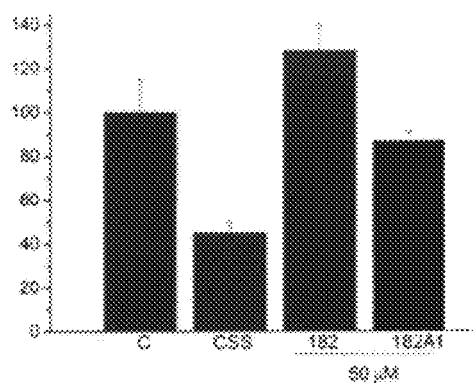
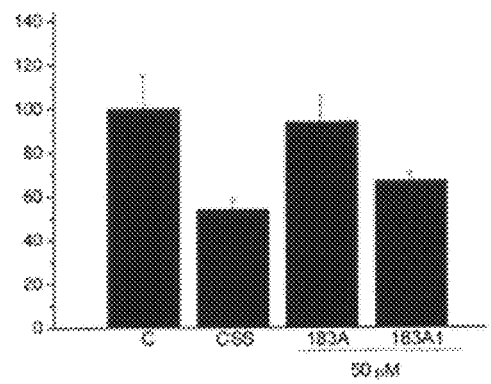
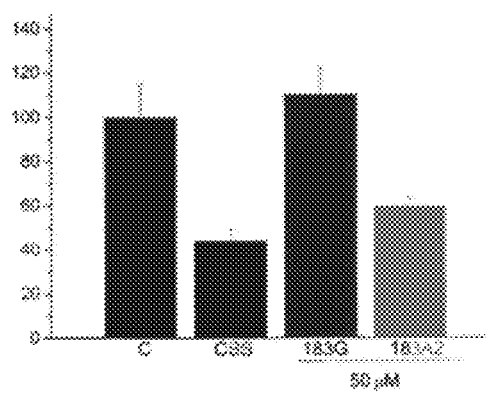
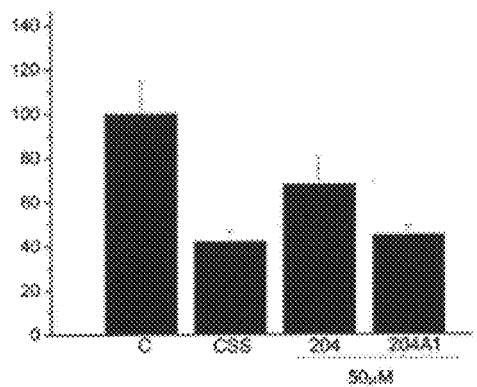
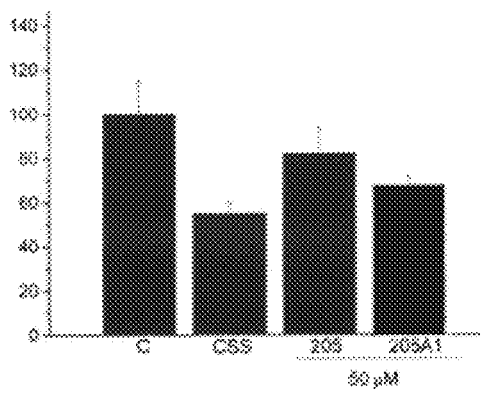
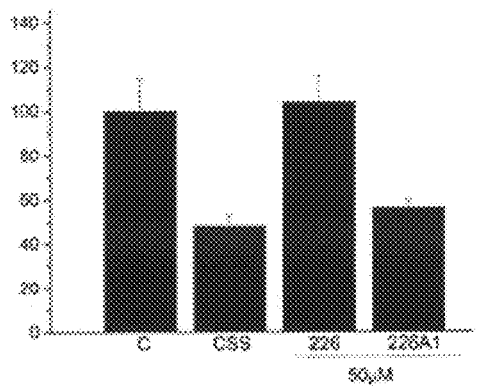

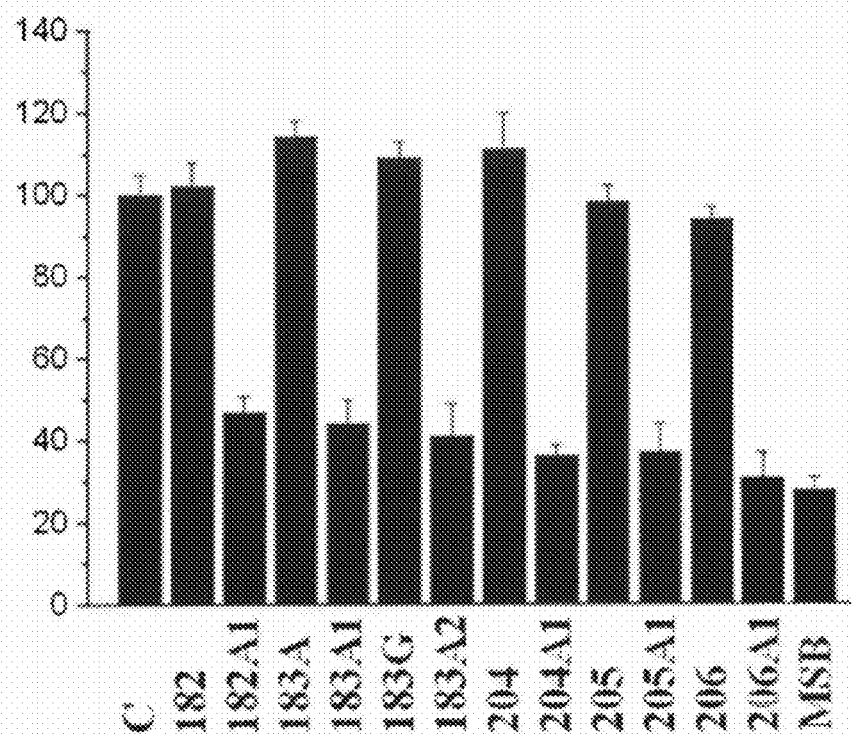
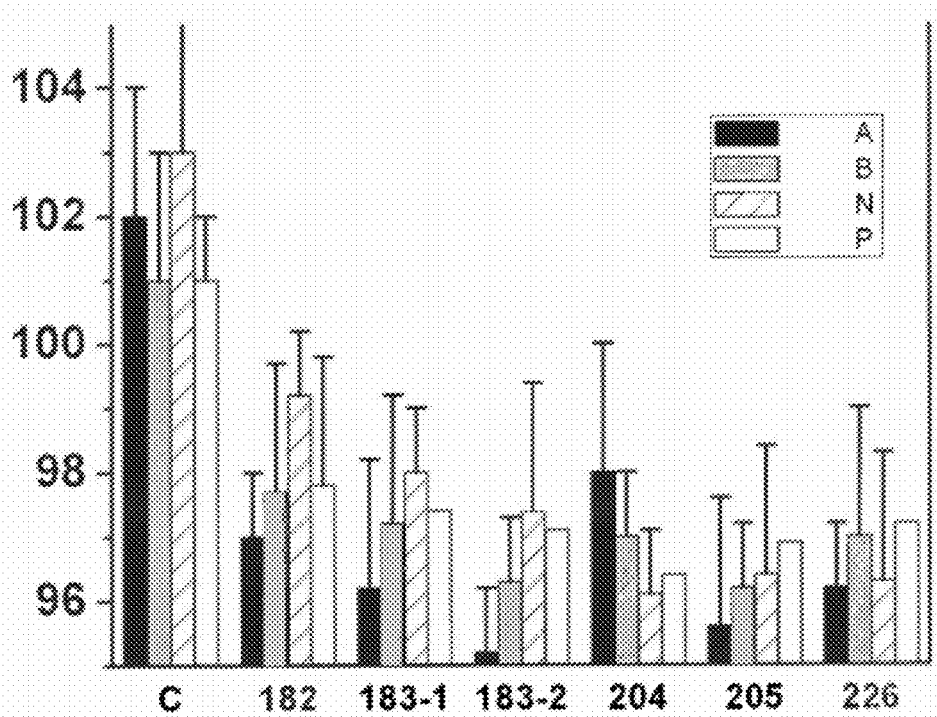
FIGURE 3

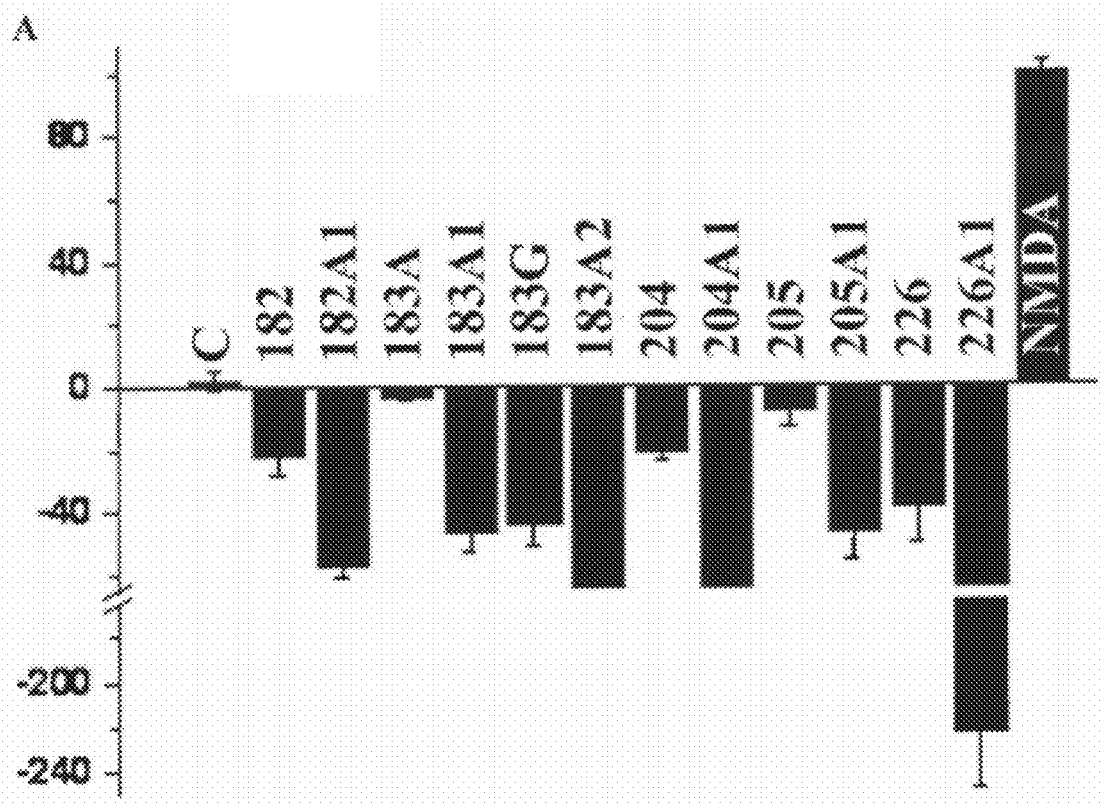
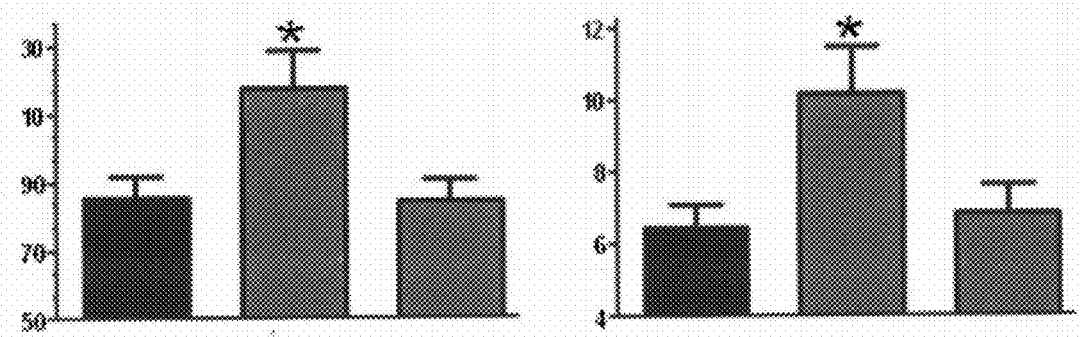

FIGURE 5
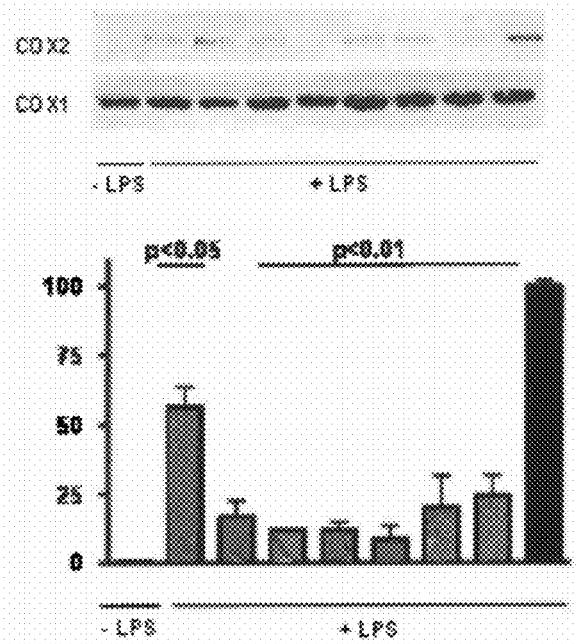
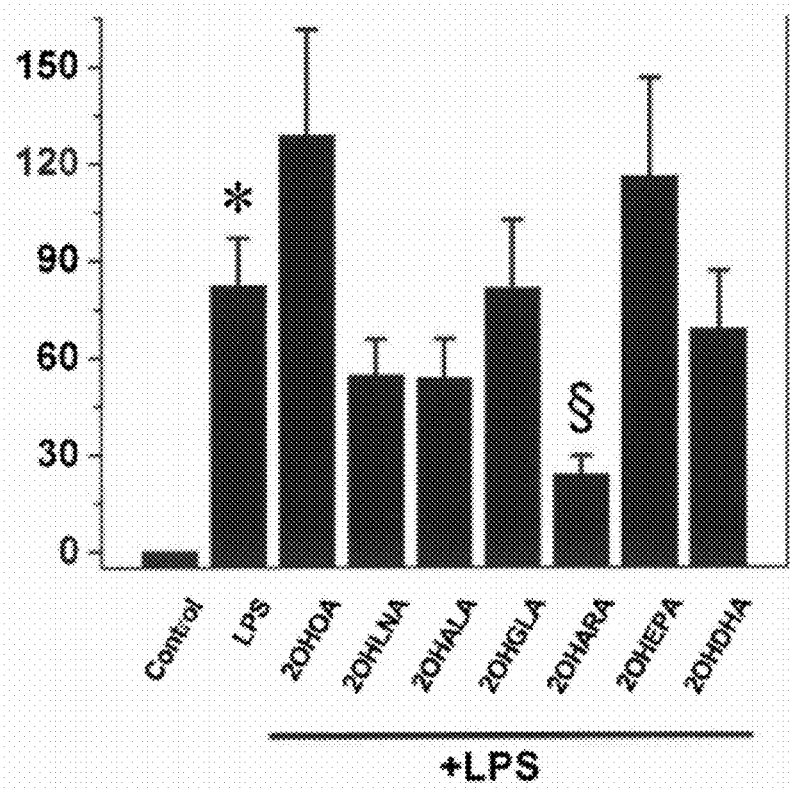

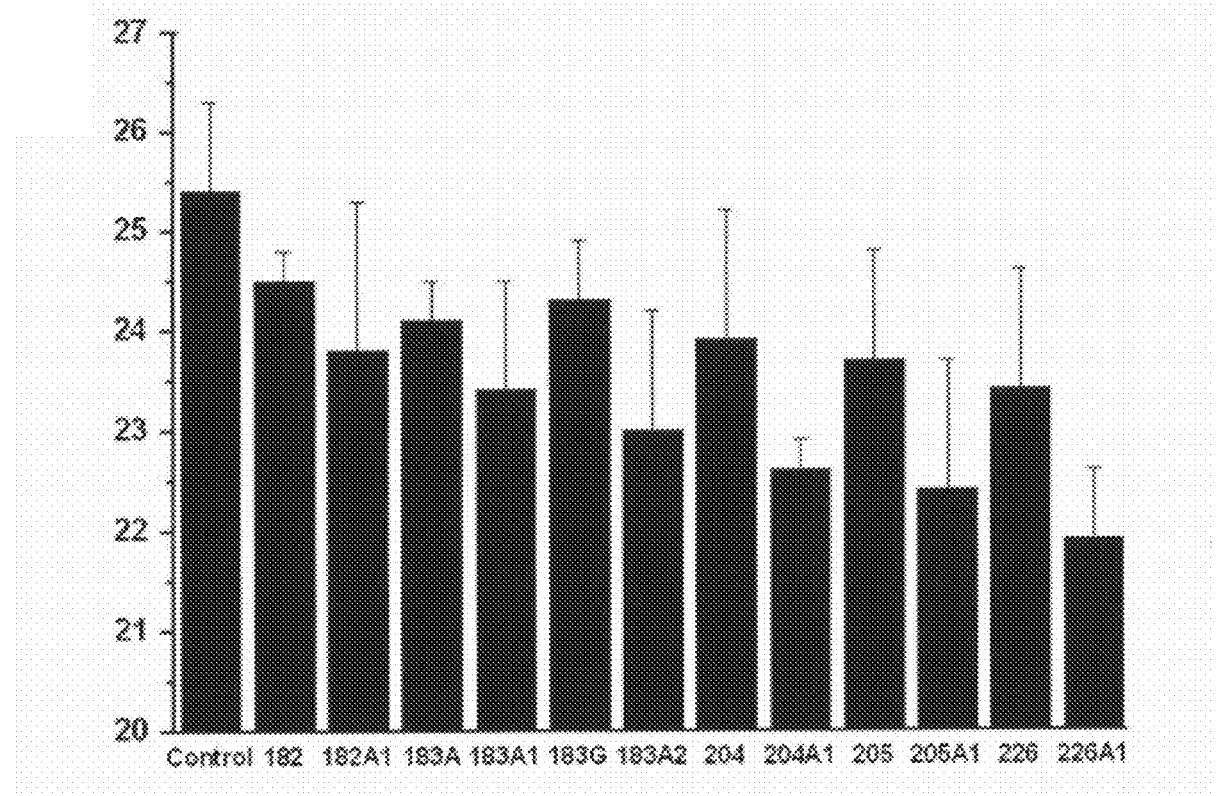

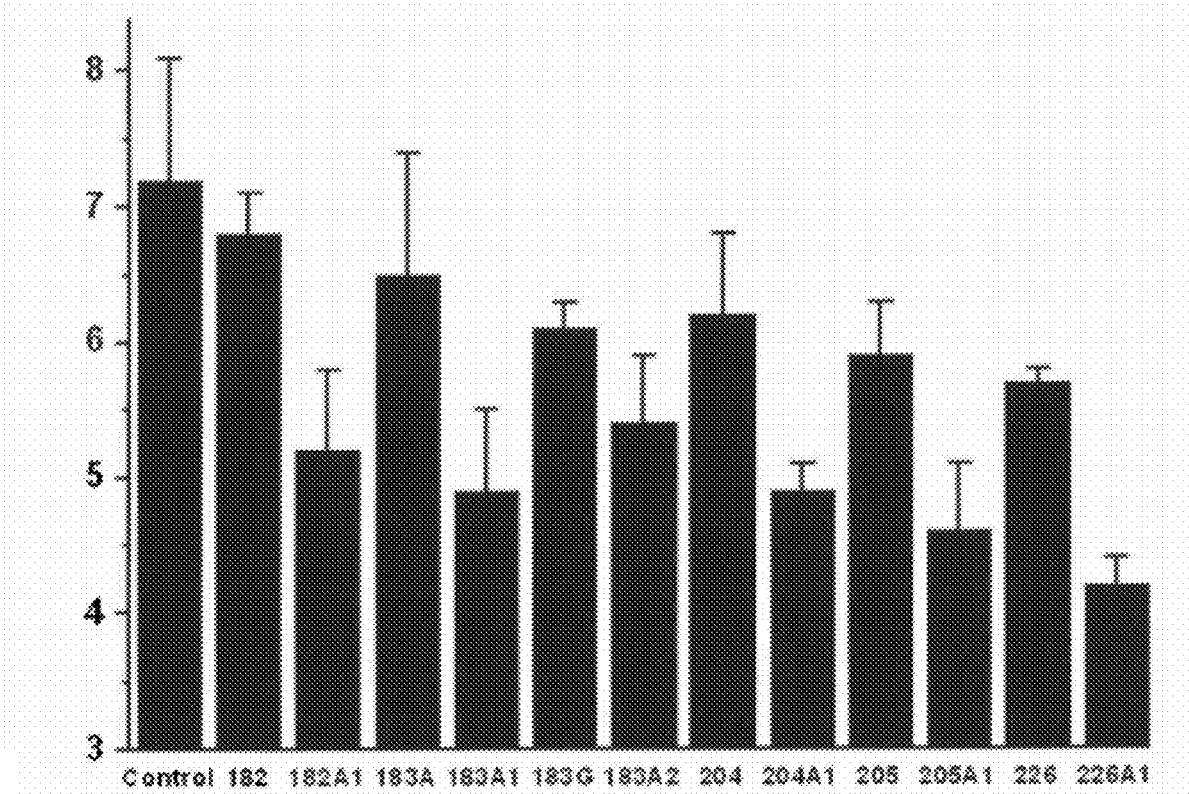

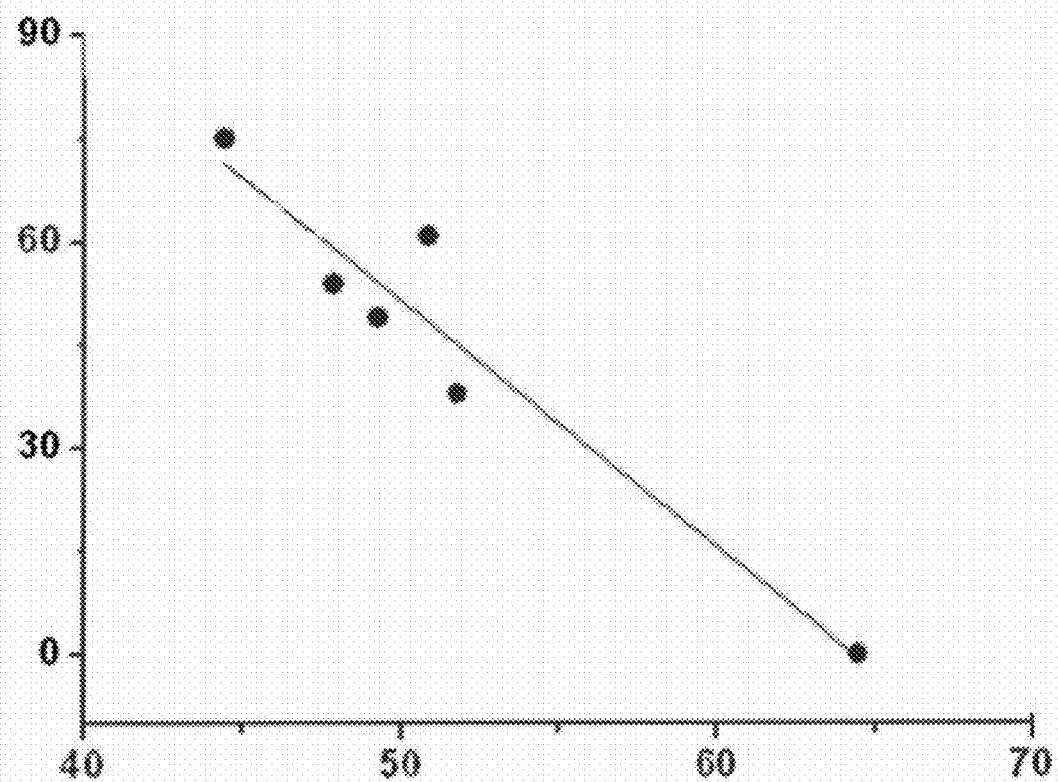

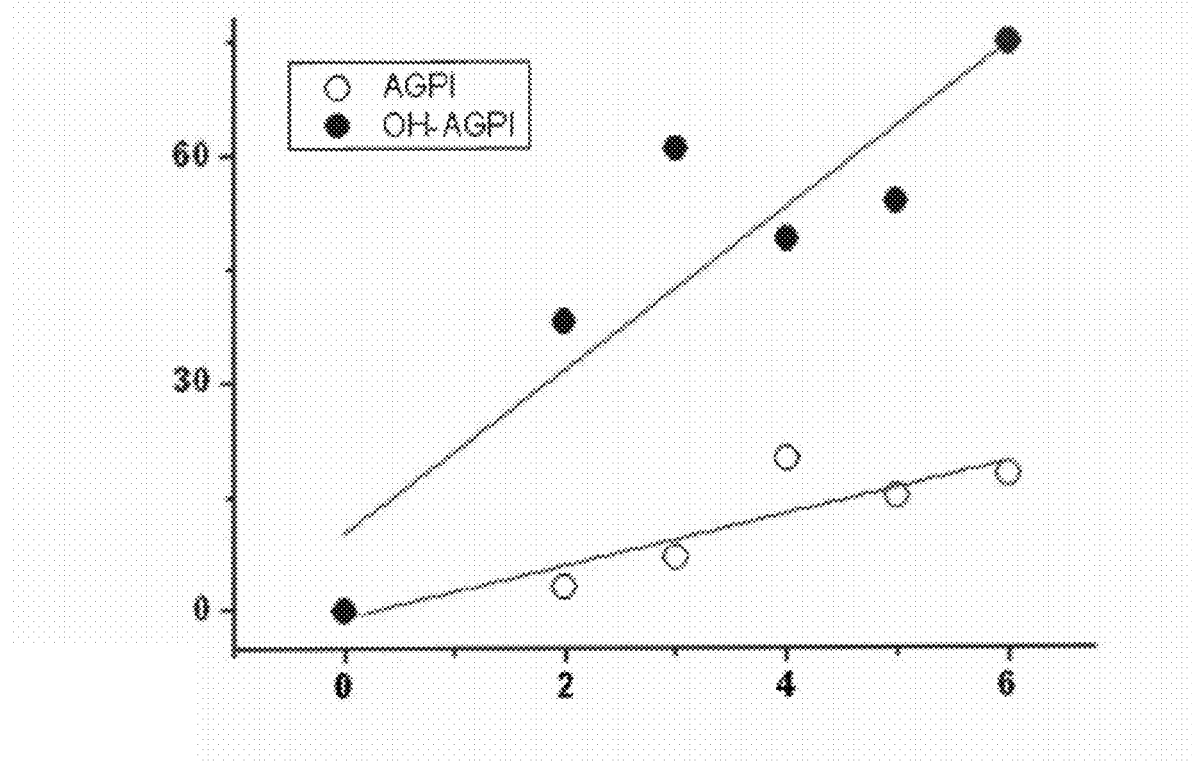

USE OF DERIVATIVES OF POLYUNSATURATED FATTY ACIDS AS MEDICAMENTS

RELATED APPLICATIONS

This application is the National Stage of International Application No. PCT/ES2010/070153, filed Mar. 15, 2010, which claims foreign priority benefit from Provisional Spanish Patent Application No. P200900725, filed on Mar. 16, 2009, both of which are incorporated herein by reference in their entireties.

FIELD OF THE INVENTION

The present invention relates to the use of 1,2-polyunsaturated fatty acid derivatives as medicaments, preferably for the treatment of diseases whose etiology is based on alterations of cell membrane lipids, such as: changes in the levels, in the composition or structure of these lipids and proteins that interact with them; as well as in the treatment of diseases where the regulation of lipid composition and membrane structure, as well as of proteins that interact with them with the result of reversion a of pathological state.

Thus, the present invention, because of its wide range of application, is likely to be generally included in the field of medicine and pharmacy.

STATE OF THE ART

Cell membranes are structures that define the organization of cells and the organelles they contain. Most biological processes occur in or around membranes. Lipids not only have a structural role, but also regulate the activity of important processes. Moreover, the regulation of the membrane lipid composition also influences the location or function of important proteins involved in controlling the cell's physiology, such as G proteins or PKC (Escribá et al., 1995, 1997, Yang et al, 2005, Martinez et al., 2005). These and other studies demonstrate the importance of lipids in controlling important cellular functions. In fact, many human diseases such as cancer, cardiovascular disease, neurodegenerative diseases, obesity, metabolic disorders, processes and inflammatory diseases, infectious diseases or autoimmune diseases, among others, have been associated with alterations in the levels or the composition of lipids in biological membranes, further demonstrating the beneficial effects that treatments with fatty acids could be used to reverse these diseases, in addition to those of the present invention, which regulate the composition and structure of membrane lipids (Escribá, 2006).

The lipids consumed in the diet regulate the lipid composition of cell membranes (Alemany et al., 2007). In addition, various physiological and pathological situations can change lipids in cell membranes (Buda et al., 1994; Escribá, 2006). As an example of a situation that induces physiological changes in membrane lipids it may be mentioned the fish living in rivers with variable temperature, whose lipids undergo important changes (changes in the quantity and types of membrane lipids) when the temperature goes down from 20° C. (summer) to 4° C. (winter) (Buda et al. 1994). These changes allow the maintenance of their functions in cell types of diverse nature. Examples of pathological processes that may influence the lipid composition are neurological disorders or drug-induced diseases (Rapoport, 2008). Therefore, one could say that membrane lipids can determine correct activity of multiple mechanisms of cell signalling.

Changes in membrane lipid composition affect cell signalling and may lead to development of disease or to reverse them (Escribá, 2006). Various studies over the past few years indicate that membrane lipids play a more relevant role than they had been assigned so far (Escribá et al., 2008). The classical view of the cell membrane assigns to lipids a purely structural role, as a support for membrane proteins, which are supposed to be the only functional elements of the membrane. The plasma membrane would have an additional role, avoiding water, ions and other molecules from entering into the cells. However, membranes have other functions of great importance in the maintenance of health, disease occurrence and healing. Since the body is sick because their cells are sick, alterations in membrane lipids produce alterations in cells and these can lead to the occurrence of diseases. Similarly, therapeutic, nutraceutical or cosmetic interventions, aimed at the regulation of the levels of membrane lipids can prevent and reverse (cure) pathological processes. In addition, numerous studies indicate that consumption of saturated and transmonounsaturated fats is related to the deterioration of health. In addition to the neurological diseases described above, vascular diseases, cancer and others have also been directly associated with membrane lipids (Stender and Dyerberg, 2004). The deterioration of an organism is manifested in the appearance of this and other types of diseases, which may include metabolic diseases, inflammation, neurodegeneration, etc.

Cell membranes are the selective barrier through which a cell receives metabolites and information from other cells and the extracellular environment that surrounds it. However, membranes develop other very import functions in cells. On the one hand, they serve as a support for proteins involved in receiving or initiating messages that control important organic functions. These messages, which are mediated by many hormones, neurotransmitters, cytokines, growth factors, etc., do activate membrane proteins (receptors), which propagate the received signal into the cell through other proteins (peripheral membrane proteins), some of which are also located at the membrane. Since (1) these systems work as amplification cascades, and (2) membrane lipids can regulate the localization and activity of these peripheral proteins, the lipid composition of membranes can have a major impact on cell's physiology. In particular, the interaction of certain peripheral proteins, such as G proteins, protein kinase C, Ras protein, etc., with the cell membrane depends on its lipid composition (Vogler et al., 2004, Vogler et al., 2008). Furthermore, the lipid composition of cell membranes is influenced by the type and amount of lipids in the diet (Escribá et al., 2003). In fact, nutraceutical or pharmaceutical lipid interventions can regulate the lipid composition of membranes, which in turn can control the interaction (and hence the activities) of important cell signalling proteins (Yang et al., 2005).

The fact that membrane lipids are able to control cell signalling, may also suppose that they are able to regulate the physiological status of cells and therefore the general state of health. In fact, both negative and positive effects of lipids on health have been described (Escribá et al., 2006; Escribá et al., 2008). Preliminary studies have shown that 2-hydroxyoleic acid, a monounsaturated fatty acid, is able to reverse certain pathological processes such as overweight, hypertension or cancer (Alemany et al., 2004, Martinez et al., 2005; Vogler et al, 2008).

Cardiovascular diseases are often associated with excessive proliferation of cells that constitute the heart and vascular tissues. This hyperproliferation results in cardiovascular deposits in the inner lumen of vessels and cavities of the cardiovascular system resulting in a wide range of diseases such as hypertension, atherosclerosis, ischemia, aneurysms, ictus, infarction, angina, stroke (cerebrovascular accidents) etc. (Schwartz et al., 1986). In fact, it has been suggested that the development of drags that prevent cell proliferation would be a good alternative for prevention and treatment of cardiovascular disease (Jackson and Schwartz, 1992).

Obesity is caused by an altered balance between intake and energy expenditure, in part due to alterations in the mechanisms regulating these processes. On the other hand, this condition is characterized by hyperplasia (increase in cell number) or hypertrophy (increased size) of fat cells, adipocytes. Numerous studies show that fatty acids either free or as part of other molecules, may influence a number of parameters related to energy homeostasis, such as body fat mass, lipid metabolism, thermogenesis and food intake, among others (Vogler et al., 2008). In this sense, the modification of fatty acids could be a strategy to regulate energy homeostasis, i.e., the balance between intake and energy expenditure, and therefore related processes such as appetite or body weight.

Neurodegenerative processes lead to a number of diseases with different manifestations, but with the common characteristic of being caused by degeneration or dysfunction of the central and/or peripheral nervous system cells. Some of these neurodegenerative processes involve a significant reduction in the cognitive ability of patients or alterations of their motor ability. Neurodegenerative, neurological and neuropsychiatric disorders have a common basis of neuronal degeneration or alteration of its components, such as lipids (e.g., myelin) or membrane proteins (e.g., adrenergic, serotonergic receptors, etc.). Such central nervous system diseases include, among others, Alzheimer's disease, Parkinson's disease, Multiple sclerosis, ALS, sclerosis of the hippocampus and other types of epilepsy, focal sclerosis, adrenoleukodystrophy and other leukodystrophy, vascular dementia, senile dementia, headaches including migraine, central nervous system trauma, sleep disorders, dizziness, pain, stroke (cerebrovascular accidents), depression, anxiety, or addictions. Furthermore, certain neurological and neurodegenerative diseases may lead to processes that end up in blindness, hearing problems, disorientation, altered mood, etc.

An example of well-characterized neurodegenerative disorder is Alzheimer's disease, characterized by the formation of senile plaques, composed of membrane protein fragments (eg β-amiloyd peptide) originated from a wrong peptide processing, followed by an accumulation on the outside of the cells, and neurofibrillary tangles of Tau protein. This process has been associated with alterations in the metabolism of cholesterol and the consequent alteration of the levels of certain membrane lipids such as cholesterol and docosahexaenoic acid (Sagin and Sozmen, 2008, Rapoport, 2008). In addition, several neurodegenerative diseases such as Parkinson's disease, Alzheimer's disease, senile dementia (or Lewy bodies) have been associated with pathological accumulation of fibrillar aggregates of the α-synuclein protein, which lead to a significant alteration of the cellular metabolism of triglycerides (Coles et al., 2001). In fact, the development of these and other neurodegenerative diseases is associated with alterations in serum or cell lipids, such as cholesterol, triglycerides, sphingomyelin, phosphatidylethanolamine, etc. This again suggests that lipids play a crucial role in the correct activity of neurons, nerves, brain, cerebellum and spinal cord, which is logical given the abundance of lipids in the central nervous system. The molecules of this invention have a high or very high potential to reverse many of the processes associated with neurological, neurodegenerative and neuropsychiatric disorders.

Moreover, different types of sclerosis and other neurodegenerative diseases related to the "demyelination", whose net result is the loss of lipids on the cover of the neuronal axons, with consequent changes in the process of propagation of electrical signals that this involves. Myelin is a fatty layer that surrounds the axons of many neurons and that is formed by a series of spiral folds of the plasma membrane of glial cells (Schwann cells). Therefore, it's clear that lipids play an important role in the development of neurodegenerative diseases. Moreover, it was found that unmodified natural PUFAs have a moderate preventive effect on the development of neurodegenerative processes (Lane and Farlow, 2005). In fact, the most important lipid in the central nervous system is docosahexaenoic acid, a natural PUFA and whose abundance is altered in many neurodegenerative processes.

Metabolic diseases form a group of diseases characterized by the accumulation or deficit of certain molecules. A typical example is accumulation of glucose, cholesterol and/or triglycerides above normal levels. The increased levels of glucose, cholesterol and/or triglycerides, both systemic (e.g., increased plasma levels) and at cellular level (e.g., in cell membranes) is associated with alterations in cell signalling leading to dysfunction at various levels, and are usually due to errors in the activity of certain enzymes or to the inadequate control of such proteins. Among the most important metabolic disease are hypercholesterolemia (high cholesterol) and hypertriglyceridemia (high triglycerides). These diseases have higher rates of incidence, morbidity and mortality, so their treatment is a necessity of first order. Other important metabolic diseases include diabetes and insulin resistance, characterized by problems in the control of glucose levels. These metabolic diseases are involved in the occurrence of other diseases, like cancer, hypertension, obesity, atherosclerosis, etc. Recently, it has been defined another disease process closely related to metabolic disorders described above and which could constitute a new type of metabolopathy per se, it is the metabolic syndrome.

The protective role of certain polyunsaturated fatty acids (PUFAs) on certain diseases has been described by different researchers. For example, PUFAs slow the development of cancer and have positive effects against the development of cardiovascular disease, neurodegenerative diseases, metabolic disorders, obesity, inflammation, etc. (Trombetta et al., 2007, Jung et al., 2008, Florent et al., 2006). These stimuli indicate the important role of lipids (PUFA) in both the etiology of various diseases and in its treatment. However, the pharmacological activity of these compounds (PUFA) is very limited due to rapid metabolism and short half-life in blood. Therefore it seems necessary to develop PUFAs with a slower metabolism, which results in an increased presence in the cell membrane compared to the PUFAs used up to now facilitating the interaction of cell signalling peripheral proteins. The molecules of this invention are synthetic derivatives of PUFAs, have a slower metabolism and a marked and significantly superior therapeutic effect compared to the natural PUFAs.

Because of the relationship between structural and functional alterations of lipids located in the cell membrane with the development of various diseases of different typology, but with an etiology unitarily related to structural and/or functional alteration of lipids in membrane cells, such as cancer, cardiovascular disease, obesity, inflammation, neurodegenerative and metabolic diseases, the present invention focuses on the use of new synthetic polyunsaturated fatty acids able to solve the technical problems associated with known fatty acids mentioned above and therefore, they are useful for treating these diseases effectively.

DESCRIPTION OF THE INVENTION

Brief Description of the Invention

This invention is focused on 1,2-derivatives of polyunsaturated fatty acids (hereinafter: D-PUFAs) for use in the treatment of common diseases whose etiology is related to structural and/or functional alterations of cell membrane lipids, or of the proteins that interact with them, particularly selected from: cancer, vascular diseases, neurodegenerative and neurological disorders, metabolic diseases, inflammatory diseases, obesity and overweight. D-PUFAs have a lower metabolic rate than natural polyunsaturated fatty acids (hereinafter: PUFA), because the presence of different atoms other than hydrogen (H) at carbons 1 and/or 2 blocks its degradation through β-oxidation. This causes significant changes in the composition of membranes, regulating the interaction of cell signalling peripheral proteins. This may lead to, for example, differences in the packaging of the surface of the membrane, modulating the anchoring of peripheral proteins that participate in the propagation of cellular messages. Thus, the D-PUFA molecules that are the subject of this invention have an activity much greater than the PUFAs, showing significantly higher effect for the pharmacological treatment of the identified diseases.

As mentioned above, the diseases treated with the D-PUFA molecules of the invention share the same etiology, which is related to structural and/or functional (or any other origin) alterations of cell membrane lipids or of the proteins that interact with them. The following diseases are listed as an example:

Cancer: liver cancer, breast cancer, leukaemia, brain cancer, lung cancer, etc.

Vascular diseases: atherosclerosis, ischemia, aneurysms, ictus, cardiomyopathy, angiogenesis, cardiac hyperplasia, hypertension, infarction, angina, stroke (cerebrovascular accident), etc.

Obesity, overweight, appetite control and cellulite.

Metabolic diseases: hypercholesterolemia, hypertriglyceridemia, diabetes, insulin resistance, etc.

Neurodegenerative diseases, neurological and neuropsychiatric disorders: Alzheimer's disease, vascular dementia, Zellweger syndrome, Parkinson's disease, multiple sclerosis, amyotrophic lateral sclerosis, hippocampal sclerosis and other types of epilepsy, focal sclerosis, adrenoleukodystrophy and other types of leukodystrophy, vascular dementia, senile dementia, dementia of Lewy, multiple systemic atrophy, prion diseases, headaches including migraine, central nervous system injury, sleep disorders, dizziness, pain, stroke (cerebrovascular accidents), depression, anxiety, addictions, memory, learning or cognitive problems and general diseases requiring stop of neurodegeneration or neuro-regeneration induced by the treatment with the compounds of the invention.

Inflammatory diseases, including inflammation, cardiovascular inflammation, tumour induced inflammation, inflammation of rheumatoid origin, inflammation of infectious origin, respiratory inflammation, acute and chronic inflammation, inflammatory nature hyperalgesia, edema, inflammation resulting from trauma or burns, etc.

The D-PUFA compounds of the present invention are characterized by the following formula (I):

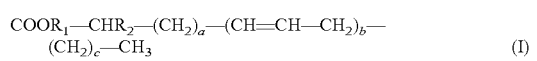

(I)

where a, b and c can have independent values between 0 and 7, and $R_1$ and $R_2$ may be an ion, atom or group of atoms with a molecular weight that independently do not exceed 200 Da.

In a preferred structure of the invention a, b and c can have independent values between 0 and 7, $R_1$ is H and $R_2$ is OH.

In another preferred structure of the invention a, b and c can have independent values between 0 and 7, $R_1$ is Na and $R_2$ is OH, In another preferred structure of the invention a and c can have independent values between 0 and 7, b can have independent values between 2 and 7, and $R_1$ and $R_2$ may be an ion, atom or group of atoms whose molecular weight is independently equal or less than 200 Da.

The administration of the fatty acids of the invention can be carried out by any means, for example enterally (IP), orally, rectally, topically, by inhalation or by intravenous, intramuscular or subcutaneous injection. In addition, the administration may be either according to the formula above or in any pharmaceutically acceptable derivative from it, such as: esters, ethers, alkyl, acyl, phosphate, sulfate, ethyl, methyl, propyl, salts, complexes, etc.

In addition the fatty acids of the invention can be administered alone or formulated in pharmaceutical or nutraceutical compositions which combine with each other and/or with excipients s such as: binders, fillers, disintegrators, lubricants, coaters, sweeteners, flavouring excipients, colouring excipients, transporters, etc. and combinations of all of them. Also, the fatty acids of the invention can be part of pharmaceutical or nutraceutical compositions in combination with other active ingredients.

For the purposes of the present invention the term "nutraceutical" is defined as a compound that is ingested regularly during feeding and acts to prevent diseases, in this case, with an etiology linked to alterations of cell membrane lipids, For the purposes of the present invention the term "therapeutically effective amount" is one that reverses or prevents the disease without showing adverse side effects.

BRIEF DESCRIPTION OF THE FIGURES

FIG. 2. Effect of certain PUFAs and D-PUFA molecules of the present invention on the proliferation of A10 vascular cells. On the y axis it is represented the number of cells (% control) depending on the fatty acid used (horizontal axis). The cells were incubated in complete medium (control, C), incomplete medium without supplement (CSS) or complete medium in the presence of PUFAs (182, 183A, 183G, 204, 205 and 226) or D-PUFAs (182A1, 183A1, 183A2, 204A1, 205A1 and 226A1). The reduction of proliferation, but still above the values of CSS, indicates that these molecules have the capacity to regulate abnormal proliferation of cardiovascular cells without being toxic.

FIG. 3

Figure 1:
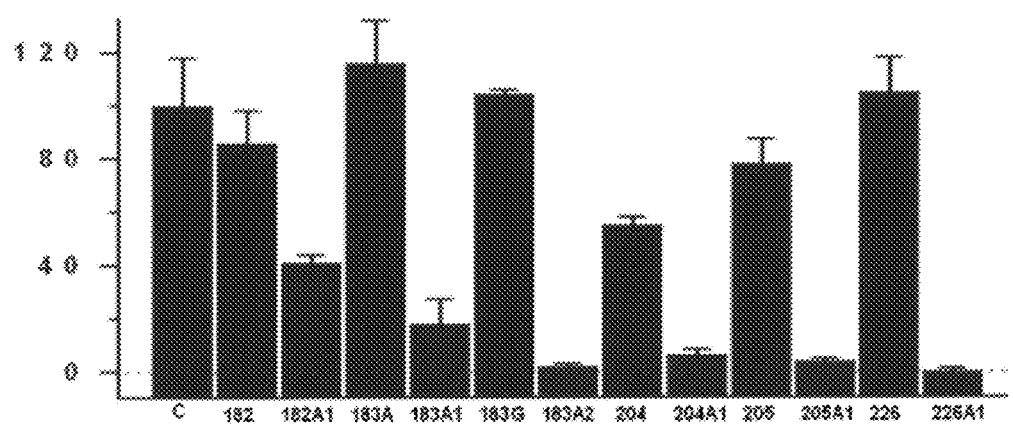
FIG. 1. Effect of compounds in Table 1 on tumour cell growth. On the y axis it is represented the number of viable cells (% control) depending on the compound used (x-axis). Human lung cancer (A549) cells were cultured in RPMI-1640 with 10% serum for 48 hours in the absence (control) or presence of 250 μM of the compounds of the invention. The graph represents the number of viable cells (mean and standard error of the mean of three experiments). The dotted line represents the total elimination of cells (0% viability).

A. Proliferation of adipocytes cultured in the absence (control, C) or presence of different D-PUFAs and PUFAs. On the y axis it is represented the number of cells (% control)

depending on the fatty acid used (x axis). As non-proliferation control, a serum deficient medium (medium with low serum percentage, MSB) was used.

B. In the Y-axis it is represented the body weight (% of untreated control) and the horizontal axis the compounds used in the treatment of experimental animals. In the X axis, from left to right, it is represented first the treatment with vehicle (C) and then, the treatment with several of the compounds of the invention. SHR rats were treated for one month with 200 mg/kg of each one or of the 24 compounds shown in the Figure. Each experimental group consisted of six animals and for each series a group of animals treated with vehicle (water) was used, and results were compared with the weight of the animals that had not received any treatment. The letters A, B, N and P indicate the combination of radicals $R_1$ and $R_2$ according to Table 3.

FIG. 4

A. Death of P19 cells cultured in the absence of external factors (control, C: 0% neuronal death) and in the presence of NMDA (100% neuronal death). On the vertical axis it is represented the neuronal death (% of control) depending on the fatty acid used (x-axis). The presence of PUFAs induced modest increases in the survival of P19 cells in the presence of NMDA. D-PUFAs induced significant increases in cell survival values, exceeding in more than 200% in the case of 226A1. Since the number of cells in cultures treated cells is higher than in control cells, it may be affirmed that these compounds not only prevent neuronal death induced by NMDA (anti-neurodegenerative) but also are neuroregenerative agents.

B. Effect of D-226B 1 PUFA in improving exercise performance in the radial maze in an animal model of Alzheimer's disease. In the Y axis of the left figure it is shown the time taken to complete the exercise and in the vertical Y axis of the right figure the total number of errors made in the implementation of programmed exercise (mean ±standard error of the mean) (runtime). In both figures, from left to right, it is represented in the X axis the results in healthy mice (control) (first column), in mice with induced Alzheimer and treated with water as vehicle (second column) or in mice treated with the compound 226B1 (third column). Animals with Alzheimer's disease took longer and made more errors than healthy mice, being the differences statistically significant (*, $P<0.05$). By contrast, mice with Alzheimer that were treated with the compound 226 B1 showed no significant differences with healthy animals.

FIG. 5

A. The upper panel is an immunoblot that shows the inhibition of the expression of the pro-inflammatory COX-2 protein, induced previously by bacterial lipopolysaccharide (LPS) (C+, 100%) in human macrophages derived from monocytes U937 by different D-PUFA of the present invention. In the lower panel, it is shown the COX-2/COX-1 relationship as % of control (Y axis) for the following compounds (X-axis): OOA (2-hydroxy-oleic acid), OLA (182A1), OALA (183A1), OGLA (183A2), OARA (204A1), OEPA (205A1), ODHA (226A1).

B. It shows anti-inflammatory efficacy of different D-PUFA compounds of the present invention in an animal model of inflammation. It shows the inhibitory effect on serum levels of TNFα (pg/ml) induced by LPS in mice (y axis) for different compounds of the invention (X axis). The reduction of this factor is directly related to the anti-inflammatory medication. The compounds are the same as in the left pane.

FIG. 6. Cholesterol levels (A) and total triglycerides (B) in 3T3-L1 cells. On the vertical axis it is represented the levels of cholesterol (A) or triglycerides (B) (% total lipids) depending on the fatty acid used (x-axis). Shown values are mean±standard error of the mean of cholesterol and triglycerides compared to the total lipids in cell membranes measured by spectrophotometric methods (cholesterol) or thin layer chromatography followed by gas chromatography (triglycerides). The graphs show the quantified values in cells cultured in the absence (Control) or presence of the D-PUFAs or PUFAs listed above.

FIG. 7

A. Relationship between the structure of membrane and cellular effects induced by D-PUFAs. It is represented in the ordinate axis the cellular effects (% control) compared to $H_{II}$ transition temperature (X-axis). The mean of the effect of each of the D-PUFA molecules was determinated (average effect of each lipid in all disease models studied and the number of double bonds) and it is plotted against the transition temperature. The reduction in $H_{II}$ transition temperature indicates a greater induction of membrane discontinuities, which results in the presence of anchoring sites in the membrane for peripheral proteins and leads to better regulation of cell signalling and, therefore, more effective for the control of certain diseases.

B. Relationship between therapeutic efficacy of PUFAs (empty circles) and D-PUFAs (solid circles.) Each point is the average of the effect observed for all diseases studied (Y axis: change with respect to control %) depending on the number of double bonds presented by each molecule (horizontal axis). In both cases the correlations were significant (P<0.05). It was observed that the therapeutic effect depends on the number of double bonds that the molecule has, which in turn is related to the ability to regulate the membrane structure. In this sense, the presence of a radical in carbons 1 and 2, present in D-PUFAs, but not in PUFAs, is essential to enhance the therapeutic effect of these molecules.

These results indicate that the effects of lipids contained in this invention have a common basis. These correlations (with $r^2$ values of 0.77 and 0.9 for D-PUFAs and P<0.05 in both cases) clearly indicate that the structure of the lipids used is the basis of its effect and that it occurs through the regulation of membrane structure, caused by the structure-function relationship of each lipid. In fact, there is a number of research works in which human diseases are associated with alterations described above in the levels of PUFAs, demonstrating the important role of lipids in cellular physiology.

DETAILED DESCRIPTION OF THE INVENTION

The broad spectrum of therapeutic applications offered by D-PUFA molecules of the present invention leads to widely assume that these D-PUFA molecules confer the membranes with specific structural properties that allow the proper processing of the activity carried out in and through these membranes. In other words, many of the abnormalities that give rise to different kinds of diseases are caused by significant variations in the levels of certain important lipids for cell function and/or of proteins that interact with membranes and/or are related to production of lipids. These pathological changes that may lead to different kinds of diseases can be prevented or reversed by synthetic fatty acids described in this invention, which can be effectively used to treat or prevent any disease whose etiology is related either to alterations in levels, composition, structure, or any other alteration of the biological membrane lipids or with a deregulation of cell signalling as a result of these changes in these lipids in biological membranes. Additionally, the lipids contained in this invention can also be used as medicines when a disease occurs as a result of another change, as long as the result of modulation of the properties and/or membrane functions is able to reverse the pathological process.

For this study of the therapeutic effects of the fatty acids of this invention, cultured cell lines and animal models of various diseases were used and the activity of D-PUFAs and PUFAs to treat different diseases was investigated.

The structure of the molecules of the invention is shown in the Tables 1, 2 and 3. Given the Formula I, compounds of the present invention preferably present combinations of the values of a, b and c shown in Table 1.

In addition, in the invention the compounds are named with a three digit number followed by the symbol X1 or X2. The number 1 denotes all D-PUFAs used, except the series based on C18:3 ω-6 (γ-linolenic acid), which appear under number 2. The first two digits of this number represent the number of carbons of the molecule. The third digit of that number represents the number of double bonds. The letter X is replaced by any of the letters from A to W (Table 3), these letters A to W to represent the specific combination of $R_1$ and $R_2$ of Formula I.

Thus, particularly preferred compound of this invention are identified under abbreviations: 182X1, 183X1, 183X2, 204X1, 205X1, 226X1 and should be interpreted according to the above directions.

TABLE 1

| D-PUFA | a | b | c |
| --- | --- | --- | --- |
| 182X1 Series | 6 | 2 | 3 |
| 183X1 Series | 6 | 3 | 0 |
| 183X2 Series | 3 | 3 | 3 |
| 204X1 Series | 2 | 4 | 3 |
| 205X1 Series | 2 | 5 | 0 |
| 226X1 Series | 2 | 6 | 0 |

Table 2 shows the structures of some of the D-PUFA molecules of the invention and the PUFAs from which they derive. As can be seen that table illustrates some compounds of the invention with different combinations of values of a, b and c, and where the radicals $R_1$ and $R_2$ are marked with the letter A, which means, as described above, that $R_1$ is H and $R_2$ is OH (see Table 3)

TABLE 2

| Name of the molecule | Structure | Prop | Abbr. |
| --- | --- | --- | --- |
| 2-hydroxy-9,12-octadecadienoic acid | COOH—CHOH—$(CH_2)_6$—$(CH=CH—CH_2)_2$—$(CH_2)_3$—$CH_3$ | S, OH | 182A1 |
| 2-hydroxy-9,12,15-octadecatrienoic acid | COOH—CHOH—$(CH_2)_6$—$(CH=CH—CH_2)_3$—$CH_3$ | S, OH | 183A1 |
| 2-hydroxy-6,9,12-octadecatrienoic acid | COOH—CHOH—$(CH_2)_3$—$(CH=CH—CH_2)_3$—$(CH_2)_3$—$CH_3$ | S, OH | 183A2 |
| 2-hydroxy-5,8,11,14-eicosatetraenoic acid | COOH—CHOH—$(CH_2)_2$—$(CH=CH—CH_2)_4$—$(CH_2)_3$—$CH_3$ | S, OH | 204A1 |
| 2-hydroxy-5,8,11,14,17-eicosapentaenoic acid | COOH—CHOH—$(CH_2)_2$—$(CH=CH—CH_2)_5$—$CH_3$ | S, OH | 205A1 |
| 2-hydroxy-4,8,11,14,17-docosahexaenoic acid | COOH—CHOH—$CH_2$—$(CH=CH—CH_2)_6$—$CH_3$ | S, OH | 226A1 |
| 9,12-octadecadienoic acid | COOH—$(CH_2)_7$—$(CH=CH—CH_2)_2$—$(CH_2)_3$—$CH_3$ | N | 182 |
| 9,12,15-octadecatrienoic acid | COOH—$(CH_2)_7$—$(CH=CH—CH_2)_3$—$CH_3$ | N | 183A |
| 6,9,12-octadecatrienoic acid | COOH—$(CH_2)_4$—$(CH=CH—CH_2)_3$—$(CH_2)_3$—$CH_3$ | N | 183G |
| 5,8,11,14-eicosatetraenoic acid | COOH—$(CH_2)_3$—$(CH=CH—CH_2)_4$—$(CH_2)_3$—$CH_3$ | N | 204 |
| 5,8,11,14,17-eicosapentaenoic acid | COOH—$(CH_2)_3$—$(CH=CH—CH_2)_5$—$CH_3$ | N | 205 |
| 4,7,10,13,16,19-docosahexaenoic acid | COOH—$(CH_2)_2$—$(CH=CH—CH_2)_6$—$CH_3$ | N | 226 |

Prop: property.
S: synthetic.
N: natural.
OH: hydroxylated on carbon 2 (α carbon).

Table 3 shows the different combinations of radicals $R_1$ and $R_2$ that can be combined with the values of a, b and c listed in Table 1.

TABLE 3

| $R_2$ \ $R_1$ | H | Na | K | $CH_3O$ | $CH_3$—$CH_2O$ | $OPO(O$—$CH_2$—$CH_3)_2$ |
| --- | --- | --- | --- | --- | --- | --- |
| OH | A | B | C | D | E | F |
| $OCH_3$ | G | | | H | I | |
| O—$CH_3COOH$ | | | | J | K | |
| $CH_3$ | | L | | M | N | |
| Cl | | | | | O | |
| $CH_2OH$ | P | | | | Q | |
| $OPO(O$—$CH_2$—$CH_3)_2$ | | | | | R | |
| NOH | | | | | S | |
| F | | | | | T | |
| HCOO | | | | U | V | |
| $N(OCH_2CH_3)_2$ | | | | | W | |

EXAMPLES

Example 1

Percentage of Total PUFAs in Membranes of Cells Treated with D-PUFAs and PUFAs Synthetic D-PUFA molecules are hydrophobic, and therefore cells exposed to these D-PUFAs have high levels of these fatty acids on their surfaces.

Table 4 shows the total percentage of PUFAs in membranes of 3T3 cells treated with 100 μM of these fatty acids for 48 hours. To perform these experiments, membranes were extracted and total fatty acids were obtained by hydrolysis in basic medium. Methanolic bases of these fatty acids were quantified by gas chromatography. The data shown are averages of four independent measures of PUFA's mass divided by the total fatty acids and expressed as a percentage. It is also shown is standard error of the mean. In cell cultures, 3T3 cells incubated in the presence of these fatty acids showed higher levels of PUFAs (including D-PUFAs) and lower levels of saturated fatty acids.

The control corresponds to a culture without the presence of added natural or synthetic fatty acids. Cells in their natural form present PUFAs in their membranes, but the presence in the medium of the D-PUFA molecules of the invention increases these levels of PUFAs in the cell membrane. Therefore these results suggest that nutraceutical or pharmaceutical interventions of these compounds of the present invention can effectively regulate the composition of the cell membranes.

TABLE 4

| Lipid added | Percentage of total PUFA |
| --- | --- |
| None (Control) | 32.4 ± 2.1 |
| 182A1 | 42.3 ± 3.1 |
| 183A1 | 42.8 ± 2.2 |
| 183A2 | 44.0 ± 2.6 |
| 204A1 | 45.5 ± 2.9 |
| 205A1 | 46.7 ± 3.4 |
| 226A1 | 48.9 ± 3.7 |

Example 2

L (Lamellar)-to-$H_{II}$ (Hexagonal) Transition in DEPE (dielaidoil phosphatidylethanolamine) Cell Membranes Tables 5 and 6 show the lamellar-to-hexagonal ($H_{II}$) transition temperature in DEPE model membranes. The transition temperature was determined by Differential Scanning Calorimetry. The proportion DEPE:D-PUFA was 10:1 (mol:mol) in all cases. Lamellar-to-hexagonal transition is an important parameter that reflects relevant signalling properties of cell membranes. The propensity to form $H_{II}$ phases, which is higher as the temperature of this transition lowers indicates that the membrane surface pressure is lower, meaning that the polar heads of phospholipids form a less dense or compact network that those formed by lamellar structures (Escribá et al., 2008). When this occurs, certain peripheral membrane proteins (such as G proteins, protein kinase C or Ras protein) can more easily bind to the membrane, while others have a poor interaction (e.g., the Gα-protein), so changes in the $H_{II}$ transition temperature are important in regulating cellular functions related to health and human therapy (Escriba et al., 1995, Vogler et al., 2004; Escriba, 2006).

Control values correspond to model membranes in the absence of fatty acids. The reduction in $H_{II}$ transition temperature obtained by using the D-PUFA of the invention indicates an increased induction of membrane discontinuities, generating anchoring sites in the membrane for peripheral proteins and leads to better regulation of cell signalling and, therefore, greater effectiveness in the control of certain diseases.

Thus Table 5 shows the transition temperature $T_H$ (hexagonal lamellar to $H_{II}$) in membranes of DEPE (4 mM) in the presence or absence of 200 μM of various compounds of the present invention of the series A.

TABLE 5

| Lipid added | Transition temperature |
| --- | --- |
| None (Control) | 64.5 |
| 182A1 | 51.8 |
| 183A1 | 51.6 |
| 183A2 | 50.1 |
| 204A1 | 49.3 |
| 205A1 | 47.9 |
| 226A1 | 44.4 |

Table 6 shows the temperature of lamellar-to-hexagonal transition in DEPE membranes in the presence of D-PUFAs from several series.

TABLE 6

|   | 182 | 183-1 | 183-2 | 204 | 205 | 226 |
| --- | --- | --- | --- | --- | --- | --- |
| B | 52.1 | 51.9 | 51.0 | 50.2 | 48.3 | 45.1 |
| D | 51.0 | 51.1 | 49.4 | 48.7 | 47.5 | 43.9 |
| E | 50.6 | 49.8 | 49.3 | 48.4 | 46.7 | 42.9 |
| G | 51.0 | 50.3 | 50.1 | 49.6 | 47.3 | 44.1 |
| O | 51.7 | 51.2 | 51.3 | 49.7 | 48.6 | 44.2 |
| R | 52.2 | 51.8 | 49.9 | 50.0 | 48.4 | 44.7 |

Example 3

Binding of $Gi_1$ Protein (Trimer) to a Model Cell Membrane

The regulation of the membrane lipid composition resulted in changes in membrane structure, as measured by Differential Scanning Calorimetry, which causes variations in the localization of G proteins in model cell membranes as shown in Table 7. The net result is a regulation of cell signalling leading to the reversal of various pathological processes, as shown later. Table 7 shows the binding of heterotrimeric $Gi_1$ protein to model membranes of phosphatidylcholine:phosphatidylethanolamine (6:4, mol:mol) measured by centrifuge analyses, followed by immunoblotting, visualization by chemiluminescence and quantified by image analysis. For these experiments it was used 2 mM phospholipid and 0.1 μM of the different D-PUFAs indicated in Table 7. The Control is a sample of model membranes in the absence of fatty acids.

These results indicate that the modification induced in the structural and functional properties of the membrane increases as the number of unsaturations increases. Both the presence of unsaturations and the changes in carbons 1 and 2 reduce the rate of metabolism of PUFAs. This fact, in relation with the particular effect of these lipids on the membrane structure, indicates that the action on the abnormal cells share a common origin.

In fact, there was a good correlation between the pharmacological effect and the effect they have on the lipid membrane structure.

TABLE 7

| Lipid added | G protein binding |
|---|---|
| None (Control) | 100 ± 5 |
| 182A1 | 312 ± 12 |
| 183A1 | 328 ± 9 |
| 183A2 | 17 ± 357 |
| 204A1 | 385 ± 22 |
| 205A1 | 406 ± 14 |
| 226A1 | 422 ± 26 |

Example 4

Use of 1,2-PUFA Derivatives for the Treatment of Cancer

Cancer is a disease characterized by the uncontrolled proliferation of transformed cells. As indicated above, in addition to certain genetic alterations, cancer is characterized by the presence of altered levels of membrane lipids that may influence cell signalling. In this sense, the natural PUFAs showed some efficacy against the development of human cancer cells (A549) at the concentrations used in this study, although its metabolic use probably prevented a greater efficacy (FIG. 1). However, D-PUFAs showed a marked and significantly higher efficacy than the unmodified molecules at carbons 1 and 2 (FIG. 1 and Table 8) at the same concentrations. These results indicate that the changes on natural polyunsaturated fatty acids results in molecules with strong anti-tumour potency and significantly greater than that of natural PUFAs and therefore have great utility in the treatment and prevention of tumour diseases through pharmaceutical and nutraceutical approaches in humans and animals.

For the experiments shown in FIG. 1, cultured human Non Small Cell Lung Cancer cells (A549) in RPMI 1640 were used, supplemented with 10% foetal bovine serum and antibiotics, at 37° C. and 5% $CO_2$. Cells were maintained in culture for 48 hours in the presence or absence of D-PUFAs and PUFAs indicated in Table 2 at a concentration of 250 µM. After treatment, cell count was performed and the study of the mechanisms involved in the antitumor activity of compounds was evaluated by flow cytometry. FIG. 1 shows the percentage of cell survival (being assigned 100% to the untreated tumour cells). These values correspond to averages of three independent experiments.

In a separate series, compounds listed in Table 3 were used against different tumour types shown in Tables 8A, 8B and 8C. These charts show the antitumor efficacy of the compounds of this invention against the growth of breast cancer cells, brain (glioma), and lung cancer. Efficacy data are expressed as $IC_{50}$ values (values of µM concentration which produce death in 50% of tumour cells) after 72 hours of incubation. The other experimental conditions are identical to those described in the preceding paragraph.

The results clearly indicate that all D-PUFAs are highly effective against tumour development. Overall, it may be seen that the series of compounds A and B are the best, so the effectiveness of these series against the development of leukaemia and liver cancer (Tables 9 and 10) was tested. Also, it can be argued that the compounds of the series 204 and 226, i.e., numbered D-PUFAs with the pair number of instaurations higher in size, are most effective. These results indicate the existence of a structure-function relationship in the pharmacological activity of the present invention, which also goes in favour of the thesis of a common mechanism of action related to the structure of each compound and, therefore, of the unity of invention in this section.

Table 8A shows the efficacy of the compounds of the invention to control the growth of breast cancer cells MDA-MB-231, expressed in micromolar $IC_{50}$ values.

TABLE 8A

| Molecule Series Subseries | 182 | 183 (1) | 183 (2) | 204 | 205 | 226 |
|---|---|---|---|---|---|---|
| A | 388 | 380 | 347 | 381 | 390 | 187 |
| B | 379 | 267 | 156 | 345 | 208 | 195 |
| C | 386 | 289 | 168 | 389 | 223 | 210 |
| D | 277 | 245 | 175 | 281 | 2 | 224 |
| E | 289 | 319 | 193 | 299 | 284 | 207 |
| F | 311 | 323 | 181 | 326 | 275 | 226 |
| G | 378 | 364 | 159 | 372 | 219 | 213 |
| H | 402 | 308 | 170 | 363 | 282 | 199 |
| I | 411 | 274 | 210 | 315 | 261 | 241 |
| J | 287 | 296 | 221 | 285 | 228 | 235 |
| K | 375 | 381 | 238 | 317 | 240 | 208 |
| L | 343 | 306 | 173 | 332 | 253 | 216 |
| M | 362 | 407 | 164 | 321 | 216 | 267 |
| N | 297 | 278 | 186 | 274 | 289 | 222 |
| O | 286 | 267 | 217 | 298 | 264 | 249 |
| P | 419 | 349 | 214 | 370 | 301 | 250 |
| Q | 328 | 312 | 205 | 306 | 247 | 263 |
| R | 371 | 305 | 172 | 285 | 245 | 204 |
| S | 388 | 291 | 189 | 293 | 270 | 211 |
| T | 391 | 290 | 216 | 317 | 233 | 199 |
| U | 410 | 344 | 228 | 369 | 272 | 227 |
| V | 442 | 326 | 241 | 352 | 298 | 215 |
| W | 391 | 311 | 203 | 311 | 256 | 246 |

Table 8B shows the efficacy of the compounds of the invention against brain cancer cell growth (glioma) U118, expressed in micromolar $IC_{50}$ values.

TABLE 8B

| Molecule Series Subseries | 182 | 183 (1) | 183 (2) | 204 | 205 | 226 |
|---|---|---|---|---|---|---|
| A | 197 | 397 | 372 | 197 | 400 | 214 |
| B | 198 | 202 | 377 | 396 | 391 | 196 |
| C | 208 | na | 379 | 287 | 442 | 237 |
| D | 221 | na | 385 | 311 | 467 | 241 |
| E | 213 | na | na | 224 | 513 | 265 |
| F | 236 | 354 | 401 | 275 | 498 | 261 |
| G | 205 | 329 | 394 | 342 | 426 | 278 |
| H | 267 | 408 | 443 | 263 | 439 | 294 |
| I | 240 | 321 | 432 | 328 | 510 | 327 |
| J | 254 | 296 | 426 | 296 | 487 | 283 |
| K | 221 | 257 | 418 | 380 | 474 | 272 |
| L | 229 | 231 | 460 | 247 | 435 | 269 |
| M | 238 | 349 | 407 | 309 | 462 | 306 |
| N | 247 | 324 | 385 | 315 | 513 | 285 |
| O | na | 370 | na | na | na | 277 |
| P | na | 285 | 389 | 291 | 432 | 290 |
| Q | na | 282 | 392 | 324 | 419 | 254 |
| R | 255 | 307 | 454 | 501 | 468 | 267 |
| S | 203 | 316 | 416 | 462 | 475 | 315 |
| T | 214 | 368 | 423 | 385 | 427 | 263 |
| U | 212 | 343 | 380 | 263 | 454 | 342 |
| V | 231 | 274 | 402 | 345 | 510 | 269 |
| W | 246 | na | 438 | 287 | 443 | 318 |

Table 8C shows the efficacy of the compounds of the invention against the growth of lung cancer cells A549, expressed in micromolar $IC_{50}$ values.

TABLE 8C

| Molecule Series Subseries | 182 | 183 (1) | 183 (2) | 204 | 205 | 226 |
|---|---|---|---|---|---|---|
| A | 944 | 200 | 192 | 243 | 394 | 195 |
| B | 196 | 195 | 197 | 413 | 202 | 198 |
| C | 635 | 281 | 241 | 521 | 325 | 214 |
| D | 541 | 326 | 267 | 372 | 364 | 221 |
| E | 387 | 294 | 243 | 475 | 413 | 209 |
| F | 354 | 347 | 259 | 392 | 338 | 286 |
| G | 439 | 273 | 295 | 427 | 407 | 273 |
| H | 462 | 319 | 219 | 398 | 290 | 247 |
| I | 673 | 348 | 276 | 459 | 351 | 298 |
| J | 321 | 281 | 259 | 362 | 416 | 215 |
| K | 274 | 276 | 2 | 414 | 275 | 250 |
| L | 385 | 285 | 283 | 326 | 362 | 221 |
| M | 286 | 322 | 248 | 375 | 293 | 208 |
| N | 329 | 379 | 255 | 420 | 384 | 236 |
| O | 452 | 344 | 318 | 461 | 418 | 264 |
| P | 328 | 317 | 272 | 387 | 339 | 291 |
| Q | 293 | 273 | 314 | 348 | 365 | 252 |
| R | 317 | 258 | 274 | 364 | 417 | 219 |
| S | 458 | 341 | 246 | 439 | 293 | 265 |
| T | 379 | 367 | 279 | 352 | 322 | 243 |
| U | 255 | 294 | 287 | 270 | 426 | 270 |
| V | 340 | 320 | 291 | 326 | 325 | 298 |
| W | 416 | 352 | 212 | 341 | 420 | 302 |

Table 9 shows the efficacy of the compounds of the invention against the development of human leukaemia (Jurkat cells) Values of $IC_{50}$ micromolar at 72 hours.

TABLE 9

| Molecule Series Subseries | 182 | 183 (1) | 183 (2) | 204 | 205 | 226 |
|---|---|---|---|---|---|---|
| A | 713 | 198 | 184 | 62 | 376 | 85 |
| B | 377 | 196 | 184 | 104 | 294 | 175 |

Table 10 shows the efficacy of the compounds of the invention against the development of liver cancer (HepG2 cells). Values of $IC_{50}$ micromolar at 72 hours.

TABLE 10

| Compound | 182 | 183 (1) | 183 (2) | 204 | 205 | 226 |
|---|---|---|---|---|---|---|
| A | 212 | 380 | 380 | 192 | 401 | 164 |

All these results indicate that the D-PUFAs are useful for the prevention and treatment of cancer included in nutraceutical and pharmaceutical compositions in humans and animals. It was also found that the potency of action of D-PUFA is correlated with the increased number of double bonds and that the presence of changes in carbon 1 and 2 is essential for the antitumor potency of the lipids to be relevant at therapeutic level. Because these compounds have anti-tumour effect against a wide range of tumour cells, it may be affirmed that they are molecules with broad anti-tumour spectrum and may be of general application against the development of any cancer.

Example 5

Use of 1,2-PUFA Derivatives for the Treatment of Cardiovascular Disease

To investigate the usefulness of the D-PUFA for the treatment of cardiovascular diseases, several experimental approaches were used. First, the efficacy of the compounds of the invention in aorta cells in culture (cell line A-10) was investigated. These cells were maintained in culture with complete medium (C, supplemented with 10% foetal bovine serum and PDGF) and incomplete medium (CSS, supplemented with 1% foetal bovine serum without PDGF). Cultures were performed for a period of 72 hours in a similar fashion as described in the preceding paragraph. After this period of incubation, cell counts were carried out by flow cytometry.

In the incomplete medium (CSS, no extra control PDGF), cells have a proliferative behaviour, similar to that produced in a healthy body. The proliferative behaviour that occurs in complete medium would be a similar situation to what occurs in a pathological organism. The presence of D-PUFA produced a significant reduction in the proliferation of normal aorta (A-10) cells in complete culture medium with proliferative agents present in the foetal serum included in the culture medium. In the presence of proliferative agents (cytokines, growth factors, etc.), A10 cell counts were similar to those obtained in incomplete medium (CSS) with the presence of the D-PUFA of the present invention (FIG. 2). In contrast, PUFA showed little or no antiproliferative efficacy, demonstrating that the changes made on these fatty acids increase substantially their pharmacological potential for treating cardiovascular diseases such as hypertension, atherosclerosis, ischemia, cardiomyopathies, aneurysms, ictus, angiogenesis, cardiac hyperplasia, infarction, angina, stroke (cerebrovascular accidents), etc.

The effects on this cell line can not be considered toxic for two reasons: (1) in complete medium, D-PUFAs never induced reductions in cell proliferation below the levels of cells incubated in incomplete medium, and (2) aorta (A10) cells treated with D-PUFAs showed no signs of molecular or cellular necrosis, apoptosis or any other type of cell death. Since the proliferation of vascular cells is involved in the development of numerous cardiovascular diseases, D-PUFAs are useful for the prevention and treatment of these diseases through nutraceutical and pharmaceutical approaches in humans and animals.

In a separate series, rat cardiomyocytes were isolated and cultured in vitro for 24 hours, after which a number of parameters were measured. First, it was measured the number, length and width of cells in culture. It was observed that all compounds of series A and B (182-226) were able to increase the number of cells that survived in culture (between 12% and 33%) and their length and width (between 18% and 42%). In addition, these compounds induce decreases in the release of lactate dehydrogenase (LDH) induced by anoxia (reductions of between 9% and 68% for all compounds of series A and B). These results indicate that the D-PUFA molecules of the present invention have a protective effect on cardiovascular cells and increase their elasticity, which can be used to prevent and treat heart and vascular diseases of various kinds, such as hypertension, atherosclerosis, ischemia, cardiomyopathy, aneurysm, ictus, angiogenesis, cardiac hyperplasia, infarction, angina, stroke (cerebrovascular accident), faulty blood circulation, etc.

In a separate experimental series, it was studied the effect of D-PUFA molecules of the present invention on blood pressure of SHR rats. In these animals both, blood pressure and levels of apolipoprotein AI (apoA-I) were measured. For these experiments Spontaneously Hypertensive Rats (SHR) were treated for 30 days with vehicle (water control) or compounds of the invention (200 mg/kg day, p.o.). At the end of this period, the animals' blood pressure and serum levels of apoA-I were measured. The results show the capacity of the compounds of the present invention to lower blood pressure and induce the expression of apoA-I, indicating that these molecules are useful in the treatment of hypertension and atherosclerosis (Table 11). For these experiments, non-invasive methods for determining blood pressure (cuff-tail method) and gene expression for apoA-I (RT-PCR) described in the literature (Terés et al., 2008) were used. The usefulness of the molecules of the present invention for the treatment of cardiovascular diseases is reinforced by its capacity for reducing the levels of serum cholesterol and triglycerides (see below).

Table 11 shows the blood pressure (mm Hg) and levels of apoA-I (%) in SHR rats. The average values of SHR before treatment were 214 mmHg and 100% respectively.

TABLE 11

| Compound | 182 | 183 (1) | 183 (2) | 204 | 205 | 226 |
|---|---|---|---|---|---|---|
| A | 204 | 201 | 189 | 205 | 193 | 194 |
|   | 146 | 134 | 311 | 131 | 346 | 324 |
| B | 201 | 197 | 182 | 202 | 187 | 186 |
|   | 178 | 151 | 285 | 144 | 264 | 333 |
| F | 198 | 203 | 191 | 199 | 195 | 202 |
|   | 192 | 146 | 279 | 163 | 319 | 357 |
| L | 207 | 205 | 194 | 197 | 198 | 200 |
|   | 131 | 125 | 268 | 188 | 376 | 296 |
| N | 187 | 208 | 194 | 201 | 189 | 199 |
|   | 159 | 189 | 296 | 174 | 293 | 348 |
| P | 202 | 201 | 187 | 203 | 194 | 193 |
|   | 184 | 178 | 347 | 153 | 337 | 382 |
| V | 207 | 199 | 198 | 198 | 191 | 195 |
|   | 166 | 152 | 282 | 161 | 315 | 324 |

Example 6

Use of 1,2-PUFA Derivatives for the Treatment of Obesity

FIG. 3A shows how PUFAs (both natural and synthetic ones) are capable of inhibiting the hyperplasia and hypertrophy of fat cells. For this study, 3T3-L1 adipocytes were used. This effect was already known and had been described previously for unmodified natural PUFAs (Hill et al., 1993). However, D-PUFAs have an increased potency to inhibit the proliferation of fat cells (FIG. 3A). This effect is not toxic in any case, since inhibition of growth of fat cells did not produce reductions in cell proliferation below levels of cells cultured in incomplete medium (with 1% serum). The cell culture media and conditions used were similar to those described above.

These results demonstrate that D-PUFAs have a high potential to inhibit the growth of fat cells and, therefore, for the prevention and treatment of obesity and other processes related to the accumulation of body adipocytes (e.g., cellulite) or appetite alterations through nutraceutical or pharmaceutical approaches in animals and humans. The observed effect, again, showed a clear correlation with the number of double bonds of the molecules used and the presence of modifications at carbons 1 and 2 in the lipid molecule.

Additionally, several compounds related to the present invention were used to study their effect on body weight of rats (FIG. 3B). In this regard, Spontaneously Hypertensive Rats (SHR) treated with compounds 182-226 (series A, B, N and P) showed reductions in body weight after 1 month treatment with 200 mg/kg (reductions of 3.2% to 6.9%) caused in part by a decrease in food intake and partly by inhibition of the proliferation of fat cells (in untreated animals fed with the same amount of food the weight drop was not as marked as in animals treated). These results demonstrate that these compounds can be used in the control of body weight (obesity and overweight), appetite control and body fat (cellulite) regulation.

Example 7

Use of 1,2-PUFA Derivatives for the Treatment of Neurodegenerative Diseases

In these studies, different models of neurodegeneration were used. First, P19 cells were studied, where neuronal differentiation was induced with trans-retinoic acid. To do this, P19 cells were incubated in minimum essential medium (α-MEM) supplemented with 10% foetal bovine serum and 2 µM of trans retinoic acid at 37° C. in the presence of 5% $CO_2$. Cells were incubated in the presence or absence of several D-PUFAs or PUFAs at different concentrations for 24 hours. Neurotoxicity was induced with 1 µM NMDA. Subsequently, the number of cells was counted by optical microscopy in the presence of trypan blue. These experiments showed that PUFAs have a protective effect on neuronal degeneration, although the effect mediated by D-PUFAs is much higher (FIG. 4A and Table 12). In this figure and table it is clear that the D-PUFA molecules of the present invention protect against neuronal death, as they inhibit NMDA-induced neuronal death, so that these substances may be useful for the prevention and treatment of neurodegenerative diseases such as Alzheimer's disease, sclerosis, Parkinson's disease, leukodystrophy, etc. It has also been shown that the number of cells in cultures treated is higher than in cultures were there are not neurodegenerative agents added. In particular, cell death negative values indicate that the number of P19 cells is higher than in a control situation. Therefore, the D-PUFA compounds of the present invention can be used to promote neuroregenerative processes, such as those produced by traumatic processes (accident) or toxic agents.

Table 12 shows the protective effect against neuronal death in P19 cells: inhibition of neuronal death (P19 cells) with D-PUFA of the present invention after treatment with NMDA (100% death). Control cells without NMDA, showed a level of 0% cell death. All percentages below 100% indicate protection against neuronal death. Negative values indicate that in addition to protection of neuronal death there is also a level of neuronal proliferation. Furthermore, the compounds of the present invention decrease the levels of α-synuclein (Table 13), a protein that is associated with neurodegenerative processes, such as Parkinson's, Alzheimer's, dementia of Lewy, multiple systemic atrophy, prion diseases, etc. Therefore, the molecules of the present invention can be applied to the prevention and treatment of neurodegenerative, neuroregenerative, neurological and neuropsychiatric processes.

TABLE 12

|   | 182 | 183-1 | 183-2 | 204 | 205 | 226 | C (NMDA) |
|---|---|---|---|---|---|---|---|
| A | −60 | −55 | −70 | −70 | −50 | −230 | 100 |
| B | −62 | −58 | −66 | −71 | −52 | −222 | 100 |
| F | −45 | −35 | −36 | −46 | −44 | −189 | 100 |
| L | −32 | −21 | −29 | −27 | −35 | −117 | 100 |
| V | −17 | −9 | −18 | −11 | −27 | −86 | 100 |

Table 13 shows the expression of α-synuclein in neuronal cultures (cells P19). C (control) represents the % of α-synuclein in untreated cells (100%).

TABLE 13

|   | 182 | 183-1 | 183-2 | 204 | 205 | 226 | C |
|---|---|---|---|---|---|---|---|
| A | 50 | 45 | 40 | 41 | 35 | 23 | 100 |
| B | 61 | 43 | 38 | 36 | 41 | 31 |   |
| F | 71 | 61 | 52 | 52 | 57 | 41 |   |
| L | 80 | 76 | 73 | 69 | 67 | 64 |   |
| V | 83 | 87 | 89 | 82 | 81 | 77 |   |

To test the efficacy of the compounds of the present invention to induce neuroregeneration or inhibit neurodegeneration, an animal model of Alzheimer's disease was used. In this model mice develop neurodegeneration because they express a series of mutant proteins that lead to brain damage (Alzh mice). B6 mice were used as healthy animal controls. Both groups of animals were treated for a period of 3 months with vehicle (water) or with various D-PUFA (20 mg/kg, daily po) since they were an age of 3 months. To determine whether cognitive improvement occurred after treatment, animal behaviour was monitored in the radial maze. The animals are kept on restricted diet to have appetite. In a symmetrical 8-arm radial maze, visual marks were placed to facilitate the orientation of the animal and food (15 mg tablet) was put in four of the arms. The time each animal took to complete the exercise, and the number of errors, were measured using a camera attached to a computer system. In this sense, Alzheimer animals have values about 50% higher than healthy animals, both by the time it takes to perform the exercise and by the number of errors made (FIG. 4B). By contrast, mice with Alzheimer treated with 226B 1 (Alzh+LP226) presented behavioural parameters similar to those of control animals and significantly ($P<0.05$) lower than animals treated with vehicle (Alzh). In this regard, the effectiveness of the compound 183B1, 205A1, 205B1, 226A1, 226 V1 was also tested, showing improvements in animals with Alzheimer's disease (times of 98, 92, 93, 86 and 89 seconds, respectively). On the other hand, it is also interesting that these same compounds (183B1, 205A1, 205B1, 226A1, 226B1 and 226V1) also produced reductions in the times taken to complete the experiment in control animals (B6 healthy mice) of 8 s, 11 s, 12 s, 18 s, 16 s and 14 s, respectively. Therefore, it may be concluded that these compounds have significant activity against neurodegeneration and in neuroregeneration. Among the neurodegenerative processes that could be prevented and treated with D-PUFA molecules of the present invention are Alzheimer's disease, Parkinson disease, Zellweger syndrome, multiple sclerosis, amyotrophic lateral sclerosis, the sclerosis of the hippocampus and other types of epilepsy, focal sclerosis, adrenoleukodystrophy and other types of leukodystrophy, vascular dementia, senile dementia, dementia of Lewy, multiple systemic atrophy, prion diseases, etc. In addition, neuroregenerative activity, evidenced by the effect in both mice with Alzheimer and healthy B6 mice, treatment can be applied to processes in which neuronal loss has occurred as a result of an accident, surgery, trauma of different nature or due to certain toxins. D-PUFA molecules of the present invention can also be used for the prevention or treatment of different neurological and/or neuropsychiatric problems, such as headaches including migraine, central nervous system injury, sleep disorders, dizziness, pain, stroke (cerebrovascular accidents), depression, anxiety, addictions, memory, learning or cognitive problems, and for enhancing the memory and cognitive ability of human beings.

Example 8

Use of 1,2-PUFA Derivatives for the Treatment of Inflammatory Diseases

Cyclooxygenase (COX) is an enzyme that can bind to membranes, taking certain lipids from there and catalyze its conversion into molecules that can have inflammatory activity. The binding of this enzyme to membrane lipids is due in part to the membrane lipid structure. The increased activity of COX 1 and 2 isoforms has been associated with the etiopathology of a number of inflammatory diseases by inhibiting arachidonic acid metabolism to produce pro-inflammatory lipid mediators. The D-PUFA compounds of the present invention produced a series of cellular signals that alter the metabolism of arachidonic acid and, as a result, they inhibit the activity and expression of COX in monocytes in culture (Table 14 and FIG. 5). Also, the D-PUFA of the present invention inhibited the production of pro-inflammatory cytokines (TNF-α) in vivo (Table 15 and FIG. 5). For this purpose, C57BL6/J mice were treated with the various derivatives (200 mg/kg, p.o.,) after inducing an inflammatory reaction in them by intraperitoneal injection of 20 μg of bacterial lipopolysaccharide (LPS). These results clearly indicate the effectiveness of the D-PUFA of the present invention to prevent or reverse inflammatory processes and pathologies.

Table 14 shows the expression of COX-2 in monocytes in culture. Inhibition of COX-2 expression in monocytes. Percentages of inhibition (compared to the positive control in the presence of LPS, 100%) of COX-2 protein levels (expression) by the various fatty acid derivatives.

TABLE 14

|   | 182 | 183-1 | 183-2 | 204 | 205 | 226 | C (LPS) |
|---|---|---|---|---|---|---|---|
| A | 24 | 20 | 23 | 17 | 31 | 23 | 100 |
| B | 39 | 33 | 29 | 28 | 39 | 37 |   |
| F | 56 | 46 | 36 | 41 | 47 | 49 |   |
| L | 67 | 65 | 48 | 47 | 53 | 69 |   |
| V | 81 | 79 | 68 | 43 | 76 | 85 |   |

Table 15 shows the production of TNF-α (%) in mice: percentage of TNF-α in serum after injection of LPS (20 μg) intraperitoneally in C57BL6/J mice (100%).

TABLE 15

|   | 182 | 183-1 | 183-2 | 204 | 205 | 226 | C (LPS) |
|---|---|---|---|---|---|---|---|
| A | 64 | 70 | 71 | 24 | 56 | 73 | 100 |
| B | 79 | 81 | 78 | 26 | 69 | 83 |   |
| F | 86 | 91 | 86 | 46 | 80 | 91 |   |
| L | 85 | 86 | 91 | 49 | 76 | 88 |   |
| V | 81 | 84 | 87 | 42 | 84 | 85 |   |

These results show that the molecules of the present invention can be useful for preventing or treating inflammatory diseases, including inflammation, cardiovascular inflammation, inflammation caused by tumours, inflammation of rheumatoid origin, inflammation caused by infection, respiratory inflammation, acute and chronic inflammation, hyperalgesia of inflammatory nature, oedema, inflammation resulting from trauma or burns, etc.

Example 9

Use of 1,2-PUFA Derivatives for the Treatment of Metabolic Diseases

Lipids are critical molecules in maintaining metabolic functions. PUFA treatments produced some modest reductions in cholesterol and triglycerides levels in 3T3-L1 cells. However, D-PUFA treatments resulted in marked and significant reductions in cholesterol and triglyceride levels in these cells. For these experiments, the above mentioned cells were incubated in RPMI 1640 medium in presence of 10% foetal bovine serum at 37° C. with 5% $CO_2$, and in the presence or absence of 150 µM of different PUFA or D-PUFA. The cells were incubated for 24 h and then subjected to lipid extraction and cholesterol and triglyceride levels were measured following the procedures described previously (Folch et al., 1951).

In a separate experimental series, SHR rats were treated with various compounds of the present invention (200 mg/kg daily, 28 days, p.o.) and the levels of cholesterol, triglycerides and glucose in serum were measured by colorimetric methods. It was observed that these compounds induce significant (and in many cases marked) reductions in the levels of these metabolites (Table 16).

The results shown in FIG. 6 and Table 16 clearly indicate that the D-PUFAs can be used as drugs for the treatment or prevention of metabolic diseases, such as hypercholesterolemia, hypertriglyceridemia, diabetes and insulin resistance in humans and animals, through pharmaceutical and nutraceutical approaches. The combination high levels of cholesterol and triglycerides, high glucose, together with cardiovascular and/or body weight alterations leads to "metabolic syndrome", which is beginning to increase in Western societies. The compounds of the present invention have great therapeutic potential for treating metabolic syndrome.

Table 16 shows the levels of cholesterol, triglycerides and glucose in SHR rats. It shows the value of cholesterol (top number), triglycerides (central number) and glucose (bottom number) in serum of SHR treated with the molecules described above (200 mg/kg daily, p.o., 28 days). Values are expressed as per cent, and in untreated (control) rats values were always considered as 100%.

TABLE 16

| Compound | 182 | 183 (1) | 183 (2) | 204 | 205 | 226 |
|---|---|---|---|---|---|---|
| A | 78 | 76 | 79 | 72 | 69 | 64 |
|   | 91 | 81 | 78 | 77 | 74 | 71 |
|   | 84 | 87 | 82 | 85 | 82 | 79 |
| B | 89 | 75 | 77 | 71 | 58 | 59 |
|   | 72 | 66 | 76 | 69 | 65 | 62 |
|   | 87 | 84 | 86 | 89 | 87 | 81 |
| F | 92 | 78 | 84 | 76 | 71 | 67 |
|   | 88 | 71 | 87 | 81 | 83 | 78 |
|   | 89 | 76 | 85 | 84 | 82 | 86 |
| L | 89 | 82 | 83 | 83 | 79 | 71 |
|   | 93 | 77 | 79 | 82 | 78 | 74 |
|   | 94 | 85 | 92 | 91 | 85 | 87 |
| N | 92 | 72 | 89 | 82 | 80 | 75 |
|   | 93 | 69 | 85 | 81 | 73 | 72 |
|   | 90 | 84 | 92 | 82 | 86 | 83 |
| V | 94 | 75 | 84 | 84 | 85 | 81 |
|   | 93 | 70 | 92 | 81 | 79 | 84 |
|   | 93 | 79 | 88 | 87 | 84 | 89 |

Example 10

Structural Basis of the Therapeutic Effects of 1,2-derivatives of PUFAs

Numerous studies have shown that the intake or treatment with lipid results in changes in the lipid composition of cell membranes. Furthermore, such composition has a direct effect on the membrane lipid structure, which in turn regulates cell signalling and is related to the occurrence of many diseases. FIG. 7 shows the correlation between changes in the structure of the membrane produced by different D-PUFAs (as measured by the $H_{II}$ transition temperature) and the cellular effects observed in this study. For this purpose, we determined the mean effect of each of the D-PUFAs (average of each lipid for all diseases studied with respect to the number of double bonds) and the results have been plotted against the transition temperature. The reduction in $H_{II}$ transition temperature indicates a greater induction of discontinuities in membranes, creating docking sites for the peripheral membrane proteins that leads to a better regulation of cell signalling, and therefore a more effective control of certain diseases. To some extent the fact that complex organisms can metabolize drugs and that some additional mechanisms may be operating in some types (subtypes) of diseases, suggests that some of the molecules with fewer double bonds can have greater pharmacological activity. However, in general, it appears that the therapeutic effect depends on the number of double bonds of the molecule, which itself is related to the capacity of regulating the structure of the membranes. In that sense, the presence of radicals in carbons 1 and/or 2, found in the D-PUFA compounds of the present invention, but not in natural PUFAs, is essential to enhance the therapeutic effect of these molecules.

These results indicate that the effects of lipids contained in this invention have a common basis. These correlations (with $r^2$ values of 0.77 and 0.9 for D-PUFAs and $P<0.05$ in both cases) clearly indicate that the structure of the lipids used is the basis of its effect and that it occurs through the regulation of membrane structure, caused by the structure-function relationship of each lipid.

Thus, the present invention relates in a first aspect to compounds of formula (I) or pharmaceutically acceptable derivatives where a, b and c independently can have values from 0 to 7 and $R_1$ and $R_2$ may be an ion, atom or group of atoms with a molecular weight not exceeding 200 Da independently, for use in the treatment of diseases based on structural alterations and/or functional characteristics of cell membrane lipids selected from: cancer, vascular disease, inflammation, metabolic diseases, obesity, neurodegenerative diseases and neurological disorders.

A second aspect of the present invention relates to the use of at least one compound of formula (I), or its pharmaceutically acceptable derivatives, where a, b and c independently may have values from 0 to 7, and $R_1$ and $R_2$ can be an ion, atom or group of atoms with a molecular weight not exceeding 200 Da independently, for the preparation of a pharmaceutical and/or nutraceutical composition for the treatment of diseases based on structural and/or functional alterations of lipids in cell membranes selected from: cancer, vascular diseases, inflammation, metabolic diseases, obesity, neurodegenerative diseases and neurological disorders.

The last aspect of the present invention relates to a method for therapeutic treatment of diseases in humans and animals whose common etiology is related to structural and/or functional alterations of the lipids located in cell membranes selected from: cancer, vascular disease, inflammation, metabolic diseases, obesity, neurodegenerative and neurological diseases, which comprises administration to the patient of a therapeutically effective amount of at least one compound of formula (I) and/or its pharmaceutically acceptable salts or derivatives, where a, b and c can have independent values between 0 and 7, and $R_1$ and $R_2$ may be an ion, atom or group of atoms with a molecular weight independently not exceeding 200 Da.

References
 Alemany et al. 2004. Hypertension, 43 249
 Alemany et al. 2007. Biochim Biophys Acta, 1768, 964
 Buda et al. 1994. Proc Natl Acad Sci U.S. A., 91, 8234
 Coles et al. 2001. J Biol Chem, 277, 6344
 Escribá et al. 1995. Proc Natl Acad Sci U.S. A., 92, 7595
 Mail et al. 1997. Proc. Natl. Acad. Sci USA., 94, 11 375
 Escriba et al 2003. Hypertension, 41, 176
 Escriba 2006. Trends Mol Med, 12, 34
 Escriba et al. in 2008. J Cell Mol Med, 12, 829
 Florent et al. 2006. J Neurochem., 96, 385
 Folch et al. 1951. J Biol Chem, 191.83
 Jackson and Schwartz 1992. Hypertension, 20, 713
 Jung et al. in 2008. Am J Clin Nutr 87, 2003S
 Lane and Farlow 2005. J Lipid Res, 46, 949
 Martinez et al. 2005. Mol Pharmacol., 67, 531
 Rapoport 2008. Postraglandins Leukot. Essent. Fatty Acids 79, 153-156
 Sagin and Sozmen 2008. J Lipid Res, 46, 949
 Schwartz et al. 1986. Circ Res 58, 427
 Stender and Dyerberg 2004. Ann Nutr Metab., 48, 61
 Terés et al., 2008. Proc. Natl. Acad. Sci USA, 105, 13 811
 Trombetta et al. 2007. Chem Biol Interact., 165, 239
 Vogler et al 2004. J. Biol Chem, 279, 36 540
 Vogler et al 2008. Biochim Biophys Act, 1778, 1640
 Yang et al.2005. Mol Pharmacol., 68, 210

The invention claimed is:

1. A compound of formula (I)

$$COOR_1-CHR_2-(CH_2)_a-(CH=CH-CH_2)_b-(CH_2)_c-CH_3 \quad (I)$$

or its pharmaceutically acceptable salts for the treatment of a disease or condition in a subject in need thereof, wherein
  (i) a can be any integer value between 0 and 7,
  (ii) b can be any integer value between 2 and 7,
  (iii) c can be any integer value between 0 to 7,
  (iv) $R_1$ is a radical selected from the group consisting of H, Na, K, $CH_3O$, $CH_3-CH_2O$ and $OPO(O-CH_2-CH_3)_2$, and,
  (v) $R_2$ is a radical selected from the group consisting of OH, $OCH_3$, $O-CH_3COOH$, $CH_3$, Cl, $CH_2OH$, $OPO(O-CH_2-CH_3)_2$, NOH, F, HCOO and $N(OCH_2CH_3)_2$,
  wherein when a=6, b=2 and c=3, and $R_2$ is OH, $R_1$ is not H, and
  wherein when a=2, b=4 and c=3, and $R_2$ is OH or $CH_3$, $R_1$ is not H, and
  wherein when a=1, b=6 and c=0, and $R_2$ is $CH_3$, $R_1$ is not H; and
  wherein when a=5, b=3 and c=3, and $R_2$ is $OCH_3$, $CH_3$, $CH_2OH$, F or HCOO, $R_1$ is not H.

2. The compound of claim 1, wherein said compound comprises a combination of values a, b and c selected from the group consisting of:
  (i) a=6, b=2, and c=3;
  (ii) a=6, b=3, and c=0;
  (iii) a=3, b=3, and c=3;
  (iv) a=2, b=4, and c=3;
  (v) a=2, b=5, and c=0; and,
  (vi) a=1, b=6 and c=0.

3. The compound according to claim 2, wherein: said compound is selected from
  COOH—CHOH—$(CH_2)_6$—(CH=CH—$CH_2)_3$—$CH_3$ (183A1),
  COOH—CHOH—$(CH_2)_3$—(CH=CH—$CH_2)_3$—$(CH_2)_3$—$CH_3$ (183A2),
  COOH—CHOH—$(CH_2)_2$—(CH=CH—$CH_2)_5$—$CH_3$ (205A1)
  COOH—CHOH—$CH_2$—(CH=CH—$CH_2)_6$—$CH_3$ (226A1), or
  the sodium salt of
  COOH—CHOH—$(CH_2)_6$—(CH=CH—$CH_2)_2$—$(CH_2)_3$—$CH_3$ (182A1),
  COOH—CHOH—$(CH_2)_6$—(CH=CH—$CH_2)_3$—$CH_3$ (183A1),
  COOH—CHOH—$(CH_2)_3$—(CH=CH—$CH_2)_3$—$(CH_2)_3$ (183A2),
  COOH—CHOH—$(CH_2)_2$—(CH=CH—$CH_2)_4$—$(CH_2)_3$—$CH_3$ (204A1)
  COOH—CHOH—$(CH_2)_2$—(CH=CH—$CH_2)_5$—$CH_3$ (205A1) or
  COOH—CHOH—$CH_2$—(CH=CH—$CH_2)_6CH_3$ (226A1).

4. The compound according to claim 1, wherein said compound is COOH—CHOH—$CH_2$—(CH=CH—$CH_2)_6$—$CH_3$ and said pharmaceutically acceptable salt is the sodium salt of COOH—CHOH—$CH_2$—(CH=CH—$CH_2)_6$—$CH_3$.

5. A method to use the compound of claim 1 for the treatment of a cancer or an inflammatory disease or condition, wherein said compound is administered to a subject in need thereof, and wherein said compound is of formula (I)

$$COOR_1-CHR_2-(CH_2)_a-(CH=CH-CH_2)_b-(CH_2)_c-CH_3 \quad (I)$$

or its pharmaceutically acceptable salts, wherein
  (i) a can be any integer value between 0 and 7,
  (ii) b can be any integer value between 2 and 7,
  (ii) c can be any integer value between 0 to 7,
  (iv) $R_1$ is a radical selected from the group consisting of H, Na, K, $CH_3O$, $CH_3-CH_2O$ and $OPO(O-CH_2-CH_3)_2$, and
  (v) $R_2$ is a radical selected from the group consisting of OH, $OCH_3$, $O-CH_3COOH$, $CH_3$, Cl, $CH_2OH$, $OPO(O-CH_2-CH_3)_2$, NOH, F, HCOO and $N(OCH_2CH_3)_2$.

6. The method of claim 5, wherein the compound is administered enterally (IP), orally, rectally, topically, by inhalation, or by intravenous, intramuscular or subcutaneous injection.

7. The method of claim 5, wherein said inflammatory disease or condition is selected from the consistin of cardiovascular inflammation, inflammation caused by tumors, inflammation of rheumatoid origin, inflammation caused by infection, respiratory inflammation, acute and chronic inflammation, hyperalgesia of inflammatory nature, oedema, and inflammation resulting from trauma or burns.

8. The method of claim 5, wherein said cancer is selected from the group consisting of lung cancer, breast cancer, brain cancer, leukemia, and liver cancer.

9. A pharmaceutical or nutraceutical composition comprising the compound of claim 1 or a pharmaceutically acceptable salt of said compound.

10. The method of claim 5, wherein said compound comprises a combination of values a, b and c selected from the group consisting of:
  (i) a=6, b=2, and c=3;
  (ii) a=6, b=3, and c=0;
  (iii) a=3, b=3, and c=3;
  (iv) a=2, b=4, and c=3;
  (v) a=2, b=5, and c=0; and,
  (vi) a=1, b=6 and c=0.

11. The method of claim 5, wherein said compound is a compound selected from
  COOH—CHOH—$(CH_2)_6$—(CH=CH—$CH_2)_2$—$(CH_2)_3$—$CH_3$ (182A1), $COOH-CHOH-(CH_2)_6-(CH=CH-CH_2)_3-CH_3$ (183A1), $COOH-CHOH-(CH_2)_3-(CH=CH-CH_2)_3-(CH_2)_3-CH_3$ (183A2), $COOH-CHOH-(CH_2)_2-(CH=CH-CH_2)_4-(CH_2)_3-CH_3$ (204A1), $COOH-CHOH-(CH_2)_2-(CH=CH-CH_2)_5-CH_3$ (205A1) or $COOH-CHOH-CH_2-(CH=CH-CH_2)_6-CH_3$ (226A1), or its pharmaceutically acceptable salts.

12. The method of claim 5, wherein said compound is $COOH-CHOH-CH_2-(CH=CH-CH_2)_6-CH_3$ (226A1) or its pharmaceutically acceptable salts.

13. The method of claim 5, wherein the $R_1$ radical is H or Na, and the $R_2$ radical is OH.

* * * * *